(12) United States Patent
Kufer et al.

(10) Patent No.: US 8,101,722 B2
(45) Date of Patent: Jan. 24, 2012

(54) LESS IMMUNOGENIC BINDING MOLECULES

(75) Inventors: Peter Kufer, Moosburg (DE); Ulla Lenkkeri-Schütz, Unterschleißheim (DE); Ralf Lutterbüse, Neuried (DE); Birgit Kohleisen, München (DE)

(73) Assignee: Micromet AG, Munich (DE)

( * ) Notice: Subject to any disclaimer, the term of this patent is extended or adjusted under 35 U.S.C. 154(b) by 827 days.

(21) Appl. No.: 10/588,734

(22) PCT Filed: Feb. 16, 2005

(86) PCT No.: PCT/EP2005/001573
§ 371 (c)(1),
(2), (4) Date: Apr. 24, 2008

(87) PCT Pub. No.: WO2005/077982
PCT Pub. Date: Aug. 25, 2005

(65) Prior Publication Data
US 2008/0213256 A1  Sep. 4, 2008

(30) Foreign Application Priority Data
Feb. 16, 2004  (EP) .................................. 04003445

(51) Int. Cl.
*C12P 21/08* (2006.01)
(52) U.S. Cl. .................................. 530/387.3; 536/23.53
(58) Field of Classification Search ................ 530/387.3; 536/23.53
See application file for complete search history.

(56) References Cited

U.S. PATENT DOCUMENTS 5,530,101 A * 6/1996 Queen et al. ................ 530/387.3
2007/0081993 A1 * 4/2007 Kufer et al. ................ 424/144.1

FOREIGN PATENT DOCUMENTS

| EP | 1 454 917 A2 | 9/2004 |
|---|---|---|
| WO | WO 94/28027 A1 | 12/1994 |
| WO | WO 96/26964 A1 | 9/1996 |
| WO | WO 9847531 A2 * | 10/1998 |
| WO | WO 99/54440 A1 | 10/1999 |
| WO | WO 2004/106381 A1 | 12/2004 |
| WO | WO 2004/106383 A1 | 12/2004 |

OTHER PUBLICATIONS

Mariuzza et al. (Annu. Rev. Biophys. Biophys. Chem. 1987; 16: 139-159).*
Jones (Pharmacogenomics Journal, 1:126-134, 2001).*
Tosatto et al (Current Pharmaceutical Design, 12:2067-2086, 2006).*
Okomaoto et al (Cancer Sci., 94(1):50-56, 2003).*
Rudikoff et al (Proc. Natl. Acad. Sci. USA 1982 vol. 79: p. 1979-1983).*
MacCallum et al. (J. Mol. Biol. Oct. 11, 1996; 262 (5): 732-745).*
Holm et al. (Mol. Immunol. Feb. 2007; 44 (6): 1075-1084).*
Mack et al (J. Imm., 158:3965-3970, 1997).*
Mack et al., "A small bispecific antibody construct expressed as a functional single-chain molecule with high tumor cell cytotoxicity," *Proc. Natl. Acad. Sci. USA*, vol. 92, No. 15, Jul. 18, 1995, pp. 7021-7025.
Alcover, et al., "Lysine 271 in the Transmembrane Domain of the T-cell Antigen Receptor β Chain is Necessary for Its Assembly with the CD3 Complex but Not for á/β Dimerization", The Journal of Biological Chemistry, vol. 265, No. 7, Mar. 5, 1990, pp. 4131-4135.

* cited by examiner

*Primary Examiner* — Misook Yu
*Assistant Examiner* — Brad Duffy
(74) *Attorney, Agent, or Firm* — Foley & Lardner LLP

(57) ABSTRACT

The present invention provides a bispecific binding molecule, wherein said molecule comprises or consists of at least two domains whereby one of said at least two domains specifically binds to/interacts with the human CD3 complex and said domain comprises an amino acid sequence of an antibody derived light chain, wherein said amino acid sequence is a particularly identified amino acid sequence comprising specific amino acid substitutions, and a second domain is or contains at least one further antigen-interaction-site and/or at least one further effector domain. The invention further provides nucleic acid molecules encoding the bispecific binding molecules of the invention, vectors comprising said nucleic acid molecules and host cells transformed or transfected with said vectors. Moreover, the invention concerns a method for the production of bispecific binding molecules of the invention and compositions comprising the bispecific binding molecules of the invention, the nucleic acid molecules of the invention or the host cells of the invention.

23 Claims, 15 Drawing Sheets

Figure 1A

Hum. anti-CD3 VL nt

Figure 2A:
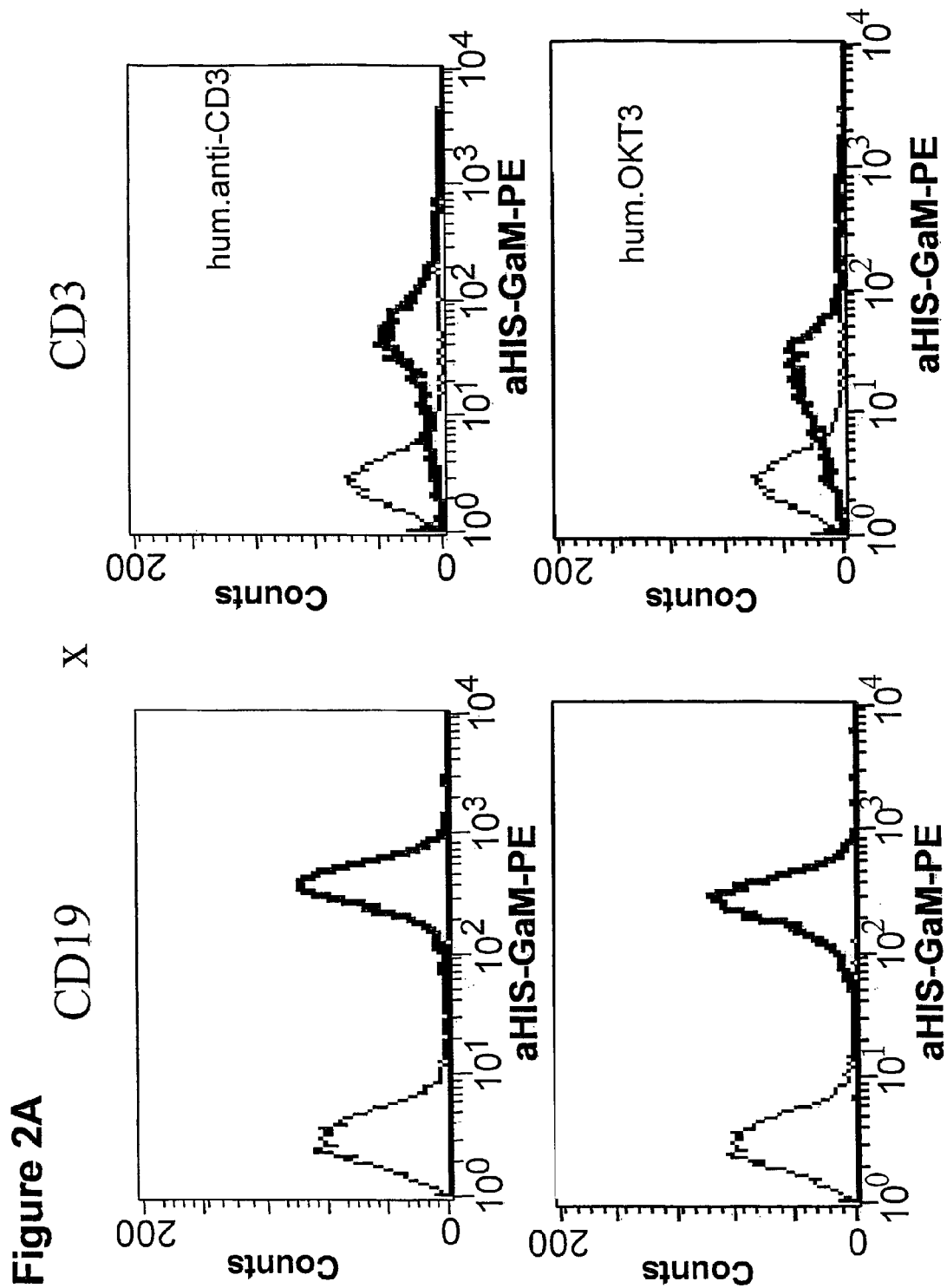

GACATCCAGATGACCCAGTCTCCATCCCTGTCTGCATCTGTAGGAGACAGAGTCACCATCA
CTTGCAGAGCAAGTCAAGGTATCAAGCGTAAGCTACATGAATTGGTATCAGCAGACACCAGGGAAAGCCCC
TAAGAGATGGATCTATGACACATCCAAAGTGGCTTCTGGGGTCCCATCAAGGTTCAGTGGCAGT
GGATCTGGGACAGATTTCACCATCACCAGCAGTCTGCAACCTGAAGATATTGCAACTTACT
ACTGTCAACAGTGGAGTAGTAACCCCTCTCACTTTTGGCCAGGGGACCAAGCTGGAGATCACC

Hum. anti-CD3 VL AA

DIQMTQSPSSLSASVGDRVTITCRASSSVSYMNWYQQTPGKAPKRWIYDTSKVASGVPSRFSGS
GSGTDYTFTISSLQPEDIATYCQQWSSNPLTFGQGTKLQIT

Hum. anti-CD3 VH nt

CAGGTGCAGCTGGTGCAGTCTGGGGGAGGCGTGGTCCAGCCTGGGGAGGTCCCTGAGACTCTCCT
GTAAGTCTTCTGGATACACCTTCACTAGCTATACGATGCACTGGGTCCGCCAGGCTCCAGGGAA
GGGGCTGGAGTGGATTGGATACATAAATCCTAGCCGTGGTTATACTAATTATAATCAGAAGGTG
AAGGACCGATTCACCATCACCAGAGACACATCCAAGAACACGGCCTTTCTGCAAATGGACAGCC
TGAGACCCGAGGACACGGCGGTGTATTTCTGTGCGAGATATTATGATGATTATTACTGCCTTGA
CTACTGGGGCCAGGGCACCCCGGTCACCGTCTCCTCA

Figure 1A (cont.)

Hum. anti-CD3 VH AA

QVQLVQSGGGVVQPGRSLRLSCKSSGYTFTRYTMHWVRQAPGKGLEWIGYINPSRGYTNYNQKV
KDRFTISRDNSKNTAFLQMDSLRPEDTGVYFCARYYDDHYCLDYWGQGTPVTVSS

Figure 1B

Figure 1B (cont.)

DIQLTQSPASLAVSLGQRATISCKASQSVDYDGDSYLNWYQQIPGQPPKLLIYDASNLVSGIPPRFSGSGSG
TDFTLNIHPVEKVDAATYHCQQSTEDPWTFGGGTKLEIKGGGGSGGGGSGGGGSQVQLQQSGAELVRPGSSV
KISCKASGYAFSSYWMNWVKQRPGQGLEWIGQIWPGDGDTNYNGKFKGKATLTADESSSTAYMQLSSLASED
SAVYFCARRETTVGRYYYAMDYWGQGTTVTVSSGGGGSGGGGSGGGGSQVQLVQSGGGVVQPGRSLRLSCKSSGYTFTRYT
MHWVRQAPGKGLEWIGYINPSRGYTNYNQKVKDRFTISRDNSKNTAFLQMDSLRPEDTGVYFCARYYDDHYC
LDYWGQGTPVTVSSVEGGSGGSGGGSGGGVDDIQMTQSPSSLSASVGDRVTITCRASSSVSYMNWYQQTPG
KAPKRWIYDTSKVASGVPSRFSGSGSGTDYTFTISSLQPEDIATYYCQQWSSNPLTFGQGTKLQIT

Figure 1C

```
TGTACACTCCGAGCTCGTGATGACACAGTCTCCATCCTCCCTGACTGTGACAGCAGGAGAGAAGGTCACTAT
GAGCTGCAAGTCCAGTCAGAGTCTGTTAAACAGTGGAAATCAAAAGAACTACTTGACCTGTACCAGCAGAA
ACCAGGGCAGCCTCCTAAACTGTTGATCTACTGGGCATCCACTAGGGAATCTGGGGTCCCTGATCGCTTCAC
AGGCAGTGGATCTGGAACAGATTTCACTCTCACCATCAGCAGTGTGCAGGCTGAAGACCTGGCAGTTTATTA
CTGTCAGAATGATTATAGTTATCCGCTTCGGTGCTGGGACCAAGCTTGAGATCAAAGGTGGTGGTGG
TTCTGGCGGCGGCGGCTCCGGTGGTGGTTCTGAGGTGCAGCTGCTCGAGCAGTCTGGGAGCTGAGCTGGT
AAGGCCTGGGACTTCAGTGAAGATATCCTGCAAGGCTTCTGGATACGCCTTCACTACTGGCTAGGTTG
GGTAAAGCAGAGGCCTGGACAAATGAGCCAAAGCCTGGAGATGGAGACAAATCTTCCCTGAAGTGGTAATATCCACTA
CAATGAGAAGTTCAAGGGCAAGGCCACACTGACTGCAGACACATCTTCTGTGCAGAGCTCAGCTGACTA
TAGCCTGACATTTGAGGACTCTGCTGTTACATCCTCCGAGGTGGCTCCCAGTGCAGCTGGTGCAGTCTGG
CTGGGCCAAGGGACCACGGTCACCGTCTCTGGAGGTGGTCCCGAGACTCTCCTGTAAGTCTCTGGATACAATAAATCCTAGCCGTGG
GGAGGGCTGGTCCAGCCTGGTCCCCAGCCTGGGAAGGGCTGAGTGGATTGGATATACATAAATCCTAGCCGTGG
TACGATGCAACTGGTTCAAGAAGGTGAAGACCGATTCACCATCTCCAGAGACAACTCCAAGAACACGGCCTT
TTATACTAATTATAATCAGAGTGTATTTCTGTGCAAGGTGAAGGTCGAGATATTATGATGATCATTA
TCTGCAAATGGGACCAGCCTGAGAAGCAGGCCACCCCGGTCACCGTCTCCTCAGTCAGTGAAAGTGGAGGTTCTGG
CTGCCTTGACTATTGGGCCAGGTTCAGTTGGAGTGGACGACCATCCAGATGACCCAGTCTCCATCTCCCTGT
TGGAAGTGGAGGTTCAGTGGAGTGGACGACATCCAGATGACCCAGTCTCCATCCTCCCTGTCTGCATCTGT
AGGAGACAGAGCCCCTAAGTCACCTGCAGAGCAAGTTCAAGCGTAAGCTGGCTTCTGGGTCCCATCAAGGTTCAGTGG
AGGGAAAGCCCCTAAGCTCACTTGCAGAGCAAGTTCAAGGTATGACACATCCAAGTGGTAGACTGAAGAAGATATTTGCAAC
CAGTGGATCTGGACAGTAGTAACCCTCTCACTTTTGGCCAGGGACCAAGCTGCAGATCACC
TCAACAGTGGCCAGGGACCAAGCTGCAGATCACC
```

Figure 1C (cont.)

ELVMTQSPSSLTVTAGEKVTMSCKSSQSLLNSGNQKNYLTWYQQKPGQPPKLLIYWASTRESGVPDRFTGSG
SGTDFTLTISSVQAEDLAVYYCQNDYSYPLTFGAGTKLEIKGGGSGGGGSGGGGSEVQLLEQSGAELVRPG
TSVKISCKASGYAFTNYWLGWVKQRPGHGLEWIGDIFPGSGNIHYNEKFKGKATLTADKSSSTAYMQLSSLT
FEDSAVYFCARLRNWDEPMDYWGQGTTVTVSSGGGGSQVQLVQSGGGVVQPGRSLRLSCKSSGYTFTRYTMH
WVRQAPGKGLEWIGYINPSRGYTNYNQKVKDRFTISRDNSKNTAFLQMDSLRPEDTGVYFCARYDDHYCLD
YWGQGTPVTVSSVEGGSGGSGGSGGSGGVDDIQMTQSPSSLSASVGDRVTITCRASSSVSYMNWYQQTPGKA
PKRWIYDTSKVASGVPSRFSGSGSGTDYTFTISSLQPEDIATYYCQQWSSNPLTFGQGTKLQIT

Figure 1D

GAGCTCGTCATGACCCAGTCTCCATCTCTTGCTGCATCTATTAATTGCAGG
GCAAGTAAGAGCATTAGCAAATATTTAGCCTGGTATCAAGAGAAACCTGGGAAAACTAATAAGCTTCTTATC
TACTCTGGATCCACTTTGCAATCTGGAATTCCATCAAGGTTCAGTGGCAGTGGATCTGGTACAGATTTCACT
CTCACCATCAGTAGCCTGGAGCCTGAAGATTTTGCAATGTATTACTGTCAACAGCATAATGAATATCCGTAC
ACGTTCGGAGGGGGGACCAAGCTTGAGATCAAAGGTGGTGGTTCTGGCGGCGGCCTCCGGTGGTGGT
GGTTCTGAGGTGCAGCTGCTCGAGCAGTCTGGAGCTGAGCTGGTAAGCCTGGGGAAACCTGGGAAGATATCC
TGCAAGGCTTCTGGATACGCCCTTCACTAACTACTGGATGCTAGGTTGGTACAGAGGCCTGGACAAGCCACA
GAGTGGATTGGAGATCTTTCCCTGGAAGTGGTAATACTCACTGCAGCCTCAGTGAGAGGTTCAGGGCAAAGCCACA
CTGACTGCAGACAAATCCTCGAGCAGCCCTTATGCAGCTATGCCAAGGACCTGAGGACTCTGCTGTC
TATTCTGTGCAAGATTGAGGAACTGGGACGAGGCTATGGACAGCTGGTGCAGTCTGGGGCCAAGGGACCACGGTCACCGTC
TCCTCGGAGGTGGTGGATCCGTGTAAGTCTTCACTAGTACAGCTGGTCACTGGGCTCCAGCCAGGCTCCA
CTGAGACTCCCTGTAAGTCTTCTGGATACAGTGGATTGGATTACATAAATCCTGGTTATATCAGAAGGTGAAG
GGGAAGGGCTGGAGTGGATTGGATACATAAATCCCAAGACAGCCTGAGACCCGAG
GACACGGGTACCACCATCTCCAGAGAAACACTCCTTGCAAATGGACAGCCTGAGACCCAGGCACC
GACACGGGTACCACCATCTCCAGAGACAAGTCCTCAGTCTACCTGCAGATTAGCAGCCTGAGACAGCC
GACACGGGTGTATTTCTGTGCGAGATATTATGATGACTGCCTTGACTATTGGGCCAGGTCAGGTGAC
CCGGTACCCGTCTCAGTCCCTGTCTCCTCAGTGAGTGGAAGTGGAAGTTGGAAGAGCACCAGTCACCTTGCAGA
GACATCCAGATGACCCAGTCTCCATCCTGTCTGTGTCTGCATCTGTAGGAGACAGAGTCACCATCACTTGCAGA
GCAAGTTCAAGCGTAAGCTACATGAATTGGTATCAGCAGAAGCCCTAAGAGATGGATCTAT
GACACATCCAAAAGTTGGCTTCTGGGGTCCCATCAAGGTTCAGTGGCAGTCTGGATCTGGGACAGATTACACTTC
ACCATCAGCAGTCTGCAACCTGAAGATATTGCAACTTACTACTGTCAACAGTGGAGTAGTAACCCTCTCACT
TTTGGCCAGGGGACCAAGCTGCAGATCACC

Figure 1D (cont.)

ELVMTQSPSYLAASPGETITINCRASKSISKYLAWYQEKPGKTNKLLIYSGSTLQSGIPSRFSGSGSGTDFT
LTISSLEPEDFAMYYCQQHNEYPYTFGGGTKLEIKGGGGSGGGGSGGGGSEVQLLEQSGAELVKPGASVKIS
CKASGYAFTNYWLGWVKQRPGHGLEWIGDLFPGSGNTHYNERFRGKATLTADKSSSTAFMQLSSLTSEDSAV
YFCARLRNWDEAMDYWGQGTTVTVSSGGGGSGGGGSGGGGSQVQLVQSGGGVVQPGRSLRLSCKSSGYTFTRYTMHWVRQAP
GKGLEWIGYINPSRGYTNYNQKVKDRFTISRDNSKNTAFLQMDSLRPEDTGVYFCARYYDDHYCLDYWGQGT
PVTVSSVEGGSGGSGGGSGGGGSGGVDDIQMTQSPSSLSASVGDRVTITCRASSSVSYMNWYQQTPGKAPKRWIY
DTSKVASGVPSRFSGSGSGTDYTFTISSLQPEDIATYYCQQWSSNPLTFGQGTKLQIT

LESS IMMUNOGENIC BINDING MOLECULES

The present invention provides a bispecific binding molecule, wherein said molecule comprises or consists of at least two domains whereby one of said at least two domains specifically binds to/interacts with the human CD3 complex and said domain comprises an amino acid sequence of an antibody derived light chain, wherein said amino acid sequence is a particularly identified amino acid sequence comprising specific amino acid substitutions, and a second domain is or contains at least one further antigen-interaction-site and/or at least one further effector domain. The invention further provides nucleic acid molecules encoding the bispecific binding molecules of the invention, vectors comprising said nucleic acid molecules and host cells transformed or transfected with said vectors. Moreover, the invention concerns a method for the production of bispecific binding molecules of the invention and compositions comprising the bispecific binding molecules of the invention, the nucleic acid molecules of the invention or the host cells of the invention.

Several documents are cited throughout the text of this specification. Each of the documents cited herein (including any manufacturer's specifications, instructions, etc.) are hereby incorporated by reference.

Since the development of genetic engineering, immune therapy has been used to treat a number of serious diseases, e.g. tumorous diseases. However, the use of antibodies derived from non-human sources leads to several problems when using as a part of a therapeutic regimen in humans.

Firstly, non-human source antibodies may cause "cytokine release syndrome (CRS)". CRS is a clinical syndrome, which has been observed following the administration of the first few doses of anti-CD3 antibodies and is related to the fact that many antibodies directed against CD3 are mitogenic. In vitro, mitogenic antibodies directed against CD3 induce T cell proliferation and cytokine production. In vivo this mitogenic activity leads to the large-scale release of cytokines, including many T cell-derived cytokines, within the initial hours after the first injection of antibody. The mitogenic capacity of CD3-specific antibodies is monocyte/macrophage dependent and it involves the production of IL-6 and IL-1β by these cells. CRS symptoms range from frequently reported mild "flu-like" symptoms to less frequently reported severe "shock-like" reactions (which may include cardiovascular and central nervous system manifestations). Symptoms include, inter alia, headache, tremor, nausea/vomiting, diarrhoea, abdominal pain, malaise and muscle/joint aches and pains, generalized weakness, cardiorespiratory events as well as neuro-psychiatric events. Severe pulmonary oedema has occurred in patients with fluid overload and in those who appeared not to have a fluid overload. (Chatenoud, 2003 Nat. Rev. Immunol. 3:123-132)

Secondly, murine antibodies were recognized by a human anti-murine-antibody humoral immune-response (HAMAs) leading to small therapeutic window (Schroff (1985) Cancer Res. 45:879-885, Shawler (1985) J. Immunol. 135:1530-1535). HAMAs are typically generated during the second week of treatment with the murine therapeutic antibody and neutralize the murine antibodies by blocking the binding to their intended target. The HAMA response can depend on the murine constant ("Fc") antibody regions or/and the nature of the murine variable ("V") regions. This host response dramatically alters the pharmacokinetic profile of the antibody, leading to a rapid clearance of the antibody and prevents repeated dosing (Reff, 2002 Cancer Control 9:152-166).

Four basic antibody strategies have been adapted to tackle the immunogenicity of therapeutic antibodies; chimerization, providing fully human V-regions, deimmunization and humanization. In chimeric antibodies, the murine constant regions are replaced with human constant regions on the basis that the constant region contributes a significant component to the immunogenicity. There are two approaches to generate fully human V-regions: selecting human antibody V-regions from a phage library and providing transgenic mice which have their own immunoglobulin genes replaced with human immunoglobulin genes. In deimmunization, specific immunogenic peptides are changed with ones having reduced or no immunogenicity according to specific algorithms.

In general, humanization entails substitutions of non-human antibody framework sequences in the variable region for corresponding human sequences, as for example is the case with CDR-grafting. The prior art describes several approaches to humanize antibodies. One of these methods is CDR grafting into foreign framework, wherein CDRs from one species are grafted into human frameworks (EP 239400). However, such humanized antibodies have often problems of insufficient binding affinity (Riechmann, 1988, Nature 332:323-327). This can be overcome by modifying the above-mentioned approach by introducing additional mutations into human frameworks. Examples where such method has been used are described in EP469167, EP 971959, EP 940468. Other approaches to humanize antibodies, are humanization by phage display (U.S. Pat. No. 5,565,322) and humanization by resurfacing/veneering, wherein surface exposed amino acids of the antibody are identified and substituted with amino acids similar or identical to human frameworks (see e.g. EP 519596, EP 592106).

Human CD3 denotes an antigen which is expressed on T cells as part of the multimolecular T cell complex and which consists of three different chains: CD3-ε, CD3-δ. and CD3-γ. Clustering of CD3 on T cells, e.g., by immobilized anti-CD3 antibodies leads to T cell activation similar to the engagement of the T cell receptor but independent of its clone-typical specificity; (see WO 99/54440 or Hoffman (1985) J. Immunol. 135:5-8).

Antibodies which specifically recognize CD3 antigen are described in the prior art, e.g. in Traunecker, EMBO J. 10 (1991), 3655-9 and Kipriyanov, Int. J. Cancer 77 (1998), 763-772. Lately, antibodies directed against CD3 have been proposed in the treatment of a variety of diseases. These antibodies or antibody constructs act as either T-cell depleting agents or as mitogenic agents, as disclosed in EP 1 025 854. Human/rodent hybrid antibodies which specifically bind to the human CD3 antigen complex are disclosed in WO 00/05268 and are proposed as immunosuppressive agents, for example for the treatment of rejection episodes following the transplantation of the renal, septic and cardiac allografts. WO 03/04648 discloses a bispecific antibody directed against CD3 and to an ovarian cancer antigen. Furthermore, Kufer (1997) Cancer Immunol Immunother 45:193-7 relates to a bispecific antibody specific for CD3 and EpCAM for the therapy of minimal residual cancer.

Several attempts to humanize an antibody binding to CD3 have been performed. U.S. Pat. No. 5,929,212, U.S. Pat. No. 5,859,205, WO 91/09968, WO 91/09967 and Adair, 1994 Hum. Antibod. Hybridomas, 5:41-48 describe a humanization method for the murine anti-human CD3 monoclonal antibody OKT3, wherein mouse (donor) CDRs are grafted into human (acceptor) frameworks and donor amino acid residues are introduced into the frameworks. U.S. Pat. No. 6,407,213 and WO 92/22653 describe a humanized UCHT1 antibody, wherein a minimum number of murine CDR and FR residues have been introduced into the context of consensus human variable domain sequences as required to achieve antigen-binding affinity and biological properties comparable to the murine parent antibody. Additional examples of humanized CD3 antibodies are EP 0626390 (OKT3), U.S. Pat. No. 5,885,573 (OKT3), U.S. Pat. No. 5,834,597 (OKT3), U.S. Pat. No. 5,585,097 (YTH 12.5) and US2002131968 (YTH 12.5).

However, it has been observed that humanized antibody constructs derived from OKT3 in the format of bispecific binding molecules have reduced specific activities such as the capacity to induce a signal via binding to/interacting with CD3.

Thus, the technical problem underlying the invention was to provide means and methods for the provision of highly efficient antibody-derived compounds which may be useful in the treatment of human diseases with reduced side-effects. In particular, the reduction of side effects is targeted, wherein the side effects are induced by the immunogenicity of the compound and result in a reduction of the activity of the compound.

The solution to said technical problem is achieved by providing the embodiments characterized in the claims.

Accordingly, the present invention relates to a bispecific binding molecule, whereby said molecule comprises or consists of at least two domains, (a) wherein one of said at least two domains specifically binds to/interacts with the human CD3 complex, wherein said domain comprises an amino acid sequence of an antibody derived light chain, wherein said amino acid sequence is
  (i) an amino acid sequence of SEQ ID NO: 2;
  (ii) an amino acid sequence encoded by a nucleic acid sequence corresponding to SEQ ID NO: 1;
  (iii) an amino acid sequence encoded by a nucleotide sequence hybridizing with the complementary strand of a nucleic acid sequence as defined in (ii) under stringent conditions; and
  (iv) an amino acid sequence encoded by a nucleic acid sequence which is degenerate as a result of the genetic code to a nucleotide sequence of any one of (ii) and (iii) with the proviso that amino acid sequences according to (i) to (iv) comprise amino acid substitutions in the CDR regions of the light chain in positions L24, L54 and L96 according to the Kabat system; and
(b) wherein a second domain is or contains at least one further antigen-interaction-site and/or at least one further effector domain.

The term "binding to/interacting with" as used in the context with the present invention defines a binding/interaction of at least two "antigen-interaction-sites" with each other. The term "antigen-interaction-site" defines, in accordance with the present invention, a motif of a polypeptide which shows the capacity of specific interaction with a specific antigen or a specific group of antigens. Said binding/interaction is also understood to define a "specific recognition". The term "specifically recognizing" means in accordance with this invention that the antibody molecule is capable of specifically interacting with and/or binding to at least two amino acids of each of the human target molecule as defined herein. Antibodies can recognize, interact and/or bind to different epitopes on the same target molecule. Said term relates to the specificity of the antibody molecule, i.e. to its ability to discriminate between the specific regions of the human target molecule as defined herein. The specific interaction of the antigen-interaction-site with its specific antigen may result in an initiation of a signal, e.g. due to the induction of a change of the conformation of the antigen, an oligomerization of the antigen, etc. Thus, specific motifs in the amino acid sequence of the antigen-interaction-site are a result of their primary, secondary or tertiary structure as well as the result of secondary modifications of said structure.

The term "specific interaction" as used in accordance with the present invention is understood to define that the CD3 specific domain of the bispecific binding molecule of the invention does not or essentially does not cross-react with (poly)peptides of similar structures. Cross-reactivity of a panel of binding molecules under investigation may be tested, for example, by assessing binding of said panel of single-chain binding molecules under conventional conditions (see, e.g., Harlow and Lane, Antibodies: A Laboratory Manual, Cold Spring Harbor Laboratory Press, 1988 and Using Antibodies: A Laboratory Manual, Cold Spring Harbor Laboratory Press, 1999) to the (poly)peptide of interest as well as to a number of more or less (structurally and/or functionally) closely related (poly)peptides. These methods may comprise, inter alia, binding studies, blocking and competition studies with structurally and/or functionally closely related molecules. These binding studies also comprise FACS analysis, surface plasmon resonance (SPR, e.g. with BIAcoree), analytical ultracentrifugation, isothermal titration calorimetry, fluorescence anisotropy, fluorescence spectroscopy or by radiolabeled ligand binding assays. Accordingly, examples for the specific interaction of an antigen-interaction-site with a specific antigen may comprise the specificity of a ligand for its receptor. Said definition particularly comprises the interaction of ligands which induce a signal upon binding to its specific receptor. Examples for corresponding ligands comprise cytokines which interact/bind with/to its specific cytokine-receptors. Another example for said interaction, which is also particularly comprised by said definition, is the interaction of an antigenic determinant (epitope) with the antigenic binding site of an antibody. Said interaction is also characterized by no or essentially no cross-reactivity of the antigenic binding site of an antibody with other epitopes of similar structures.

It is understood that the definition of the term "binding to/interacting with" comprises a binding/interacting of the binding domain to/with linear epitopes as well as a binding to/interacting with conformational epitopes, which may also be designated as structural epitope or discontinuous epitope. The definition of corresponding epitopes is known in the art. Said epitopes e.g. may consist of two regions of the human target molecules or parts thereof. In context of this invention, a conformational epitope is defined by two or more discrete amino acid sequences separated in the primary sequence which come together on the surface of the molecule when the polypeptide folds to the native protein (Sela, (1969) Science 166, 1365 and Layer, (1990) Cell 61, 553-6).

The term "discontinuous epitope" is particularly understood in context of the invention to define non-linear epitopes that are assembled from residues from distant portions of the polypeptide chain. These residues come together on the surface when the polypeptide chain folds into a three-dimensional structure to constitute a conformational/structural epitope.

The binding molecules of the present invention are also envisaged to specifically bind to/interact with at least one binding domain with a conformational epitope(s) composed of and/or comprising at least two regions of the human CD3 complex, or composed of/comprising individual components, like CD3-$\epsilon$, CD3-$\delta$ and CD3-$\gamma$ and/or combinations of said components, such as CD3-$\epsilon$/CD3-$\delta$ or CD3-$\epsilon$/CD3-$\gamma$. Furthermore, it is envisaged that said conformational/structural epitope(s) described herein comprises individual parts/ regions/stretches of at least two regions of a single component of the human CD3 complex, preferably at least two parts/regions/stretches of CD3-ε, even more preferably of the extracellular domain of CD3-ε.

As defined herein above a second domain of the bispecific binding molecule of the invention binds to at least one further antigen-interaction-site and/or at least one further effector domain. The term "effector domain" characterizes in the context of the present invention a domain of the molecule of the invention which initiates a biological effect such as the induction of a primary or secondary stimulation signal, the induction of a cytotoxic effect (including apoptosis inducing signals) or merely having the ability to specifically bind to/interact with a specific antigen-interaction-site. "Cytotoxic effect" also comprises cellular cytotoxicity exerted by T cells. Accordingly, the bispecific binding molecule of the invention is characterized by at least two different specificities.

Specificity can be determined experimentally by methods known in the art and methods as disclosed and described herein. Such methods comprise, but are not limited to Western blots, ELISA-, RIA-, ECL-, IRMA-tests and peptide scans. The term "CDR" as employed herein relates to "complementary determining region", which is well known in the art. The CDRs are parts of immunoglobulins that determine the specificity of said molecules and make contact with specific ligand.

Chothia (1987; J. Mol. Biol. 196, 901-917) and Chothia (1989; Nature, 342, 877-883).

The "Kabat system" means in the context of the present invention the standard for numbering the residues in a consistent manner according to Kabat (1991; Sequences of Proteins of Immunological Interest, 5.sup.th edit., NIH publication no. 91-3242U.S. Department of Health and Human services) and Chothia (1987; J. Mol. Biol. 196, 901-917). This numbering system is widely used by the skilled artisans and is based on sequence variability and three dimensional loops of the variable domain region which are important in antigen binding activity. All the residues of the light chains or heavy chains have distinct Kabat positions; i.e. the Kabat numbering system applies to CDRs as well as to frameworks. The positions of specific residues of any antibody may be numbered according to Kabat. The numbering system and Kabat positions of specific residues of antibodies are indicated in www.bioinf.org.uk/abs. For example, the position L24 as mentioned in the invention means the residue 24 in the light chain according to Kabat system. Accordingly, L54 and L96 refer to positions 54 and 96 in the light chain of the antibody according to the Kabat system.

The rules to identify the CDR regions of VH and VL chains according to Kabat are shown in www.bioinf.org.uk/abs and in Table 1.

TABLE 1

Identification of the CDRs in the heavy chain (CDR-H regions) and in the light chain (CDR-L regions)

| | | |
|---|---|---|
| CDR-H1 | Start | Approx residue 26 (always 4 after a Cys) [Chothia/AbM definition]; Kabat definition starts 5 residues later |
| | Residues before | always Cys-XXX-XXX-XXX |
| | Residues after | always a Trp. Typically Trp-Val, but also, Trp-Ile, Trp-Ala |
| | Length | 10 to 12 residues [AbM definition]; Chothia definition excludes the last 4 residues |
| CDR-H2 | Start | always 15 residues after the end of Kabat/AbM definition) of CDR-H1 |
| | Residues before | typically Leu-Glu-Trp-Ile-Gly (SEQ ID NO: 37), but a number of variations |
| | Residues after | Lys/Arg-Leu/Ile/Val/Phe/Thr/Ala-Thr/Ser/Ile/Ala |
| | Length | Kabat definition 16 to 19 residues; AbM (and recent Chothia) definition ends 7 residues earlier |
| CDR-H3 | Start | always 33 residues after end of CDR-H2 (always 2 after a Cys) |
| | Residues before | always Cys-XXX-XXX (typically Cys-Ala-Arg) |
| | Residues after | always Trp-Gly-XXX-Gly |
| | Length | 3 to 25 residues |
| CDR-L1 | Start | Approx residue 24 |
| | Residue before | always a Cys |
| | Residue after | always a Trp. Typically Trp-Tyr-Gln, but also, Trp-Leu-Gln, Trp-Phe-Gln, Trp-Tyr-Leu |
| | Length | 10 to 17 residues |
| CDR-L2 | Start | always 16 residues after the end of L1 |
| | Residues before | generally Ile-Tyr, but also, Val-Tyr, Ile-Lys, Ile-Phe |
| | Length | always 7 residues (except NEW (7FAB) which has a deletion in this region) |
| | Start | always 16 residues after the end of L1 |
| CDR-L3 | Start | always 33 residues after end of L2 (except NEW (7FAB) which has the deletion at the end of CDR-L2) |
| | Residue before | always Cys |
| | Residues after | always Phe-Gly-XXX-Gly |
| | Length | 7 to 11 residues |

The CDRs are the most variable part of the molecule and contribute to the diversity of these molecules. There are three CDR regions CDR1, CDR2 and CDR3 in each V domain. CDR-H characterizes a CDR region of a variable heavy chain and CDR-L relates to a CDR region of a variable light chain. H means the variable heavy chain and L means the variable light chain. The CDR regions of an Ig-derived region may be determined as described in Kabat (1991; Sequences of Proteins of Immunological Interest, 5$^{th}$ edit., NIH Publication no. 91-3242 U.S. Department of Health and Human Services), In accordance with this invention, a framework region relates to a region in the V domain (VH or VL domain) of immunoglobulins and T-cell receptors that provides a protein scaffold for the hypervariable complementarity determining regions (CDRs) that make contact with the antigen. In each V domain, there are four framework regions designated FR1, FR2, FR3 and FR4. Framework 1 encompasses the region from the N-terminus of the V domain until the beginning of CDR1, framework 2 relates to the region between CDR1 and CDR2, framework 3 encompasses the region between CDR2 and CDR3 and framework 4 means the region from the end of CDR3 until the C-terminus of the V domain; see, inter alia, Janeway, Immunobiology, Garland Publishing, 2001, 5th ed. Thus, the framework regions encompass all the regions outside the CDR regions in VH or VL domains.

The person skilled in the art is readily in a position to deduce from a given sequence the framework regions and, the CDRs; see Kabat (1991) Sequences of Proteins of Immunological Interest, 5th edit., NIH Publication no. 91-3242 U.S. Department of Health and Human Services, Chothia (1987). J. Mol. Biol. 196, 901-917 and Chothia (1989) Nature, 342, 877-883.

According to the present invention "bispecific binding molecules" are (poly)peptides which necessarily specifically bind with one domain to the human CD3 complex and/or its individual components. The term "(poly)peptide" as used herein describes a group of molecules which comprise the group of peptides, as well as the group of polypeptides. The group of peptides consists of molecules with up to 30 amino acids, the group of polypeptides consists of molecules with consisting of more than 30 amino acids. Most preferably, said "bispecific binding molecules" are selected from the group of antibodies, antibody fragments, antibody derivatives, specific binding peptides and specific binding proteins. Said antibody fragments are known in the art and comprise, but are not limited to, Fab-fragments, F(ab')$_2$ fragments, Fv fragments and the like. Antibody derivatives comprise but are not limited to labeled antibodies/antibody fragments as well as chemically modified antibody molecules/antibody fragments. As will be detailed below, particularly preferred derivatives of antibodies in the context of this invention are scFv's.

One domain of the bispecific binding molecule of the invention is derived from a humanized CDR-grafted CD3-antibody. The term "humanized" as used herein in the context with antibodies and antibody constructs may be defined as substitution of non-human sequences with corresponding human sequences. This can be achieved by grafting murine CDRs into human framework or replacing single murine amino acids in the framework with single human amino acids at the corresponding position. The term humanization as used in the invention additionally encompasses introduction of further mutations in order to improve the binding or cytotoxic activity of the protein. These further mutations need not necessarily be replacements of murine residues to human residues.

Methods for the substitution of amino acids and, particularly, of amino acids in specific positions by specifically selected amino acids in a given amino acid sequence are known to the person skilled in the art and represent standard laboratory methods. An example of such a method is primer mutagenesis (Sambrook et al. 1989).

It has been surprisingly found that humanized CD3 specific antibody constructs which comprise additional amino acid substitutions in the CDRs of the light chain, as described herein above, in the context of bispecific binding molecules have cytotoxic activity. These molecules have the capacity to induce cell death in target cells. In contrast humanized CD3 specific antibody constructs described in the art, e.g. in Adair, 1994 Hum. Antibod. Hybridomas, 5:41-48, show significantly impaired capacity to induce cell death in target cells when said constructs are expressed in the context of above defined bispecific binding molecules.

Figure 6:
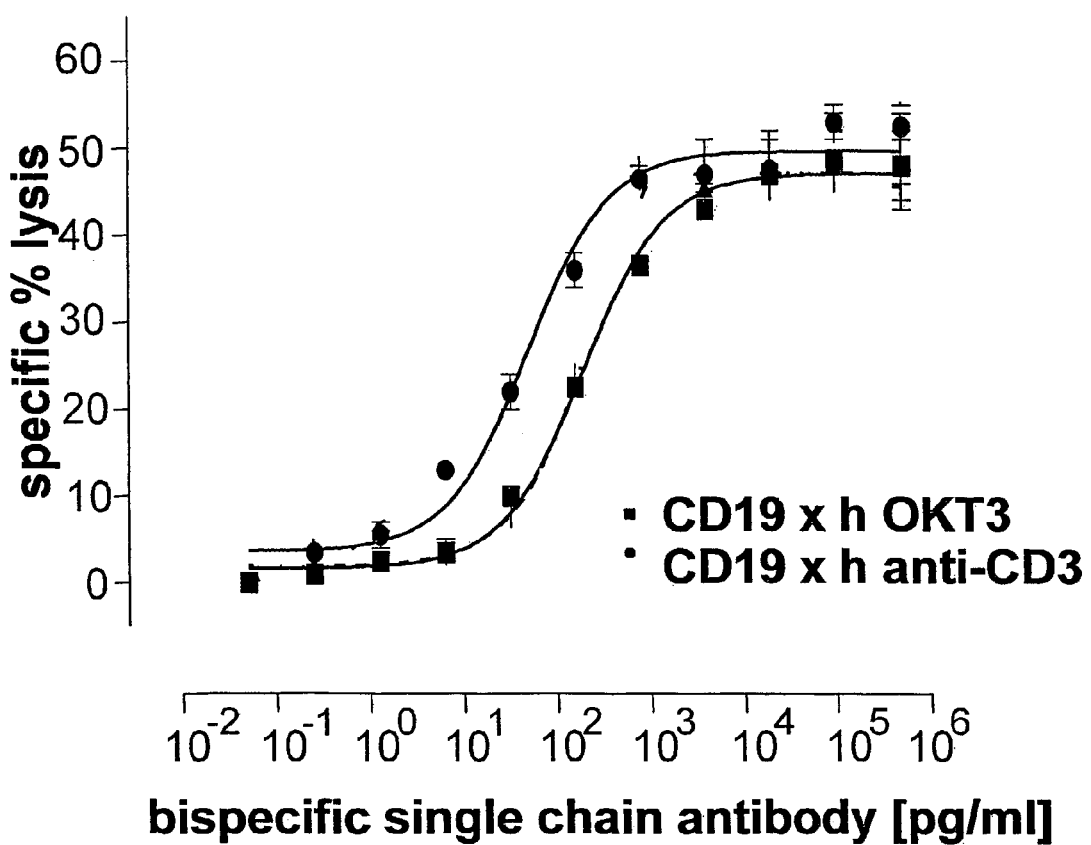

In particular, the bispecific molecule of the invention shows significant binding to its specific epitopes (see Example 4, FIG. 2) and high cytotoxic activity (Example 6, FIG. 6). The bispecific humanized CD3 of the invention with substitutions in the CDRs of the light chain of the CD3 binding part shows and EC50 value of 50 pg/ml whereas the EC50 value of the bispecific antibody construct comprising the humanized OKT3 described in Adair, 1994 Hum. Antibod. Hybridomas, 5:41-48 is 195 pg/ml. Due to the four-fold increase in cytotoxic activity the bispecific molecule of the invention may be used effectively in therapeutic activities. Furthermore, provision of a humanized bispecific molecule having high cytotoxic activity demonstrates a major advantage in the medical field because low amounts of the bispecific molecule of the invention are needed to reach therapeutic effect for patients. Thus, the bispecific molecules of the invention provide an important advantage over the prior art antibodies when treating patients since they show at the same time a high cytotoxic activity and are less immunogenic due to humanization. They therefore offer a clear improvement in the medical field.

The bispecific binding molecule of the invention differs from the humanized molecules described in the art by the above described three amino acid substitutions in CDRs of the light chains.

Since antibodies bind to/interact with its specific antigens via intramolecular forces which are affected by the particular amino acid sequences of the CDRs, a person skilled in the art would not have substituted amino acids in the amino acid sequence of the CDR region in order to increase biologic activity of the antibody. Instead the skilled person would have retained the original murine CDR sequence. Therefore, it is surprising that the bispecific binding molecule of the invention has such high cytotoxic activity.

It is particularly preferred that the domain which binds to/interacts with the human CD3 complex is characterized by having a serine at position L24, a valine at position L54 and a leucine at position L96. The position L24 means the position 24 in the light chain as described in Kabat (1991; Sequences of Proteins of Immunological Interest, 5.sup.th edit., NIH publication no. 91-3242 U.S. Department of Health and Human services) and Chothia (1987; J. Mol. Biol. 196, 901-917) and in www.bioinf.org.uk/abs. Similarly, the positions L54 and L96 represent the residues 54 and 96, respectively, of the light chain as described by Kabat and Chothia.

The bispecific binding molecule of the invention is further characterized in one embodiment that said CDR region of the light chain comprises the amino acid sequence of SEQ ID NOs: 4, 6 or 8 or encoded by a nucleic acid sequence of SEQ ID NOs: 3, 5 or 7.

It is envisaged by the invention that the domain which binds to/interacts with the human CD3 complex is a scFv.

The term "scFv" (single-chain Fv) is well understood in the art. ScFv's are preferred in context of this invention, due to their small size and the possibility of recombinantly producing these antibody derivative.

It is further envisaged, that the domain of the bispecific binding molecule of the invention which binds to/interacts with the human CD3 complex comprises or consists of the amino acid sequence of SEQ ID NO: 10 (light chain of the humanized CD3 binding molecule of the invention) or is encoded by a nucleic acid sequence of SEQ ID NO: 9.

Preferably the binding molecule of the invention is a binding molecule, wherein the domain which binds to/interacts with the human CD3 complex comprises or consists of the amino acid sequence as depicted in SEQ ID NO.: 14 or encoded by a nucleic acid sequence of SEQ ID NO: 13.

It is further envisaged by the invention that the bispecific binding molecule is a binding molecule, wherein said second domain is at least one further antigen-interaction-site specific for one or more cell surface molecule(s).

The term "cell surface molecule" as used herein denotes molecules which are presented or/and attached on/to the surface of a cell. Examples for said cell surface molecules are membrane and transmembrane proteins (including modified variants, such as glycosylated variants), molecules attached to said proteins or the cell surface as well as glycosylated moieties such as for example glycolipids. Attachment is to be understood as being effected preferably by way of an integral membrane protein, a GPI-linked (glycosyl phosphatidyl inositol-linked) protein, a proteinaceous or non-proteinaceous moiety bound covalently or non-covalently to another carrier molecule such as sugar moieties or ganglioside moieties. Preferably said cell surface molecule(s) is/are (a) tumor-specific molecule(s). A tumor-specific molecule is a tumor-associated cell surface antigen which is either found exclusively on tumor cells or is overexpressed on tumor cells as compared to non-malignant cells. Tumor-associated cell surface antigens can be expressed not only on tumor cells but also on cells/tissue which are/is not essential for survival or which can be replenished by stem cells not expressing tumor-associated cell surface antigen. Furthermore, tumor-associated cell surface antigen can be expressed on malignant cells and non-malignant cells but is better accessible by a therapeutic agent of interest on malignant cells. Examples of overexpressed tumor-associated cell surface antigens are HER-2/neu, EGF-Receptor, HER-3 and HER-4. An example of a tumor-associated cell surface antigen which is tumor specific is EGFRV-III. An example of a tumor-associated cell surface antigen which is presented on a cell which is non-essential for survival is PSMA. Examples of tumor-associated cell surface antigens which are presented on cells which are replenished are CD19, CD20 and CD33. An example of a tumor-associated cell surface antigen which is better accessible in a malignant state than in a non-malignant state is EpCAM.

Preferably, said second domain which is at least one further antigen-interaction-site is an antibody-derived region comprises a polypeptide sequence which corresponds to at least one variable region of an antibody. More preferably, said second domain is a further scFv. A particularly preferred molecular format of the invention provides a polypeptide construct in the format of a bispecific single chain antibody construct wherein the antibody-derived region comprises one VH and one VL region. VH and VL regions may be ordered in any arrangement.

The term "bispecific single chain antibody construct" relates to a construct comprising one domain consisting of (at least one) variable light chain as defined above capable of specifically interacting with/binding to human CD3/human CD3 complex and comprising a second domain consisting of (at least one) variable region(s) (or parts thereof) as defined above capable of specifically interacting with/binding to a further antigen. A part of a variable region may be at least one CDR ("Complementary Determining Region"), most preferably at least the CDR3 region. Said two domains/regions in the single chain antibody construct are preferably covalently connected to one another as a single chain. This connection can be effected either directly (domain1 interacting with CD3—domain2 interacting with the further antigen or domain1 interacting with the further antigen—domain2 interacting with CD3) or through an additional polypeptide linker sequence (domain1—linker sequence—domain2 or domain2—linker sequence—domain1). In the event that a linker is used, this linker is preferably of a length and sequence sufficient to ensure that each of the first and second domains can, independently from one another, retain their differential binding specificities. Most preferably and as documented in the appended examples, the "bispecific single chain antibody construct" is a bispecific single chain Fv (bscFv). The molecular format of bispecific single chain molecules is known in the art and is described e.g. in WO 99/54440, Mack, J. Immunol. (1997), 158, 3965-3970, Mack, PNAS, (1995), 92, 7021-7025; Kufer, Cancer Immunol. Immunother., (1997), 45, 193-197; Loffler, Blood, (2000), 95, 6, 2098-2103; Bruhl, Immunol., (2001), 166, 2420-2426. Particular examples for such bispecific single chain antibody constructs of the invention are provided herein below and illustrated in the appended examples.

In accordance with the invention are bispecific binding molecules, wherein said second domain specifically binds to/interacts with an antigen selected from the group consisting of EpCAM, CCR5, CD19, HER-2, HER-3, HER-4, EGFR, PSMA, CEA, MUC-1 (mucin), MUC2, MUC3, MUC4, MUC5AC, MUC5B, MUC7, bhCG, Lewis-Y, CD20, CD33, CD30, ganglioside GD3, 9-O-Acetyl-GD3, GM2, Globo H, fucosyl GM1, Poly SA, GD2, Carboanhydrase IX (MN/CA IX), CD44v6, Sonic Hedgehog (Shh), Wue-1, Plasma Cell Antigen, (membrane-bound) IgE, Melanoma Chondroitin Sulfate Proteoglycan (MCSP), CCR8, TNF-alpha precursor, STEAP, mesothelin, A33 Antigen, Prostate Stem Cell Antigen (PSCA), Ly-6 desmoglein 4, E-cadherin neoepitope, Fetal Acetylcholine Receptor, CD25, CA19-9 marker, CA-125 marker and Muellerian Inhibitory Substance (MIS) Receptor type II, sTn (sialylated Tn antigen; TAG-72), FAP (fibroblast activation antigen), endosialin, EGFRvIII, L6, SAS, CD63, TF-antigen, Cora antigen, CD7, CD22, Igα, Igβ, gp100, MT-MMPs, F19-antigen and CO-29.

According to a preferred embodiment of the invention said second domain specifically binds to/interacts the CD19 molecule.

It is particularly envisaged that the bispecific binding molecule of the invention which specifically binds to/interacts with the CD3 and the CD19 molecule is characterized in that said second domain comprises or consists of an amino acid sequence selected from the group of:
(a) an amino acid sequence corresponding to SEQ ID NO.: 16 or 18;
(b) an amino acid sequence encoded by a nucleic acid sequence corresponding to SEQ ID NO.: 15 or 17;
(c) an amino acid sequence encoded by a nucleic acid sequence hybridizing with the complementary strand of a nucleic acid sequence as defined in (b) under stringent hybridization conditions; and
(d) an amino acid sequence encoded by a nucleic acid sequence which is degenerate as a result of the genetic code to a nucleotide sequence of any one of (b) and (c).

More preferably, the bispecific binding molecule comprises or consists of an amino acid sequence selected from the group of:
(a) an amino acid sequence corresponding to SEQ ID NO.: 20;
(b) an amino acid sequence encoded by a nucleic acid sequence corresponding to SEQ ID NO.: 19;
(c) an amino acid sequence encoded by a nucleic acid sequence hybridizing with the complementary strand of a nucleic acid sequence as defined in (b) under stringent hybridization conditions; and
(d) an amino acid sequence encoded by a nucleic acid sequence which is degenerate as a result of the genetic code to a nucleotide sequence of any one of (b) and (c).

Said bispecific binding molecule is preferably a bispecific scFv construct, whereby a first scFv specifically binds to/interacts with CD3 and a second scFv specifically binds to/interacts with CD19.

According to a preferred embodiment of the invention said second domain specifically binds to/interacts with the EpCAM molecule.

It is particularly envisaged that the bispecific binding molecule of the invention which specifically binds to/interacts with the CD3 and the EpCAM molecule is characterized in that said second domain comprises or consists of an amino acid sequence selected from the group of:
(a) an amino acid sequence corresponding to SEQ ID NO.: 22, 24, 26, 28, 30 or 32;
(b) an amino acid sequence encoded by a nucleic acid sequence corresponding to SEQ ID NO.: 21, 23, 25, 27, 29 or 31;
(c) an amino acid sequence encoded by a nucleic acid sequence hybridizing with the complementary strand of a nucleic acid sequence as defined in (b) under stringent hybridization conditions; and
(d) an amino acid sequence encoded by a nucleic acid sequence which is degenerate as a result of the genetic code to a nucleotide sequence of any one of (b) and (c).

More preferably, the bispecific binding molecule comprises or consists of an amino acid sequence selected from the group of:
(a) an amino acid sequence corresponding to SEQ ID NO.: 34 or 36;
(b) an amino acid sequence encoded by a nucleic acid sequence corresponding to SEQ ID NO.: 33 or 35;
(c) an amino acid sequence encoded by a nucleic acid sequence hybridizing with the complementary strand of a nucleic acid sequence as defined in (b) under stringent hybridization conditions; and
(d) an amino acid sequence encoded by a nucleic acid sequence which is degenerate as a result of the genetic code to a nucleotide sequence of any one of (b) and (c).

Said bispecific binding molecule is preferably a bispecific scFv construct, whereby a first scFv specifically binds to/interacts with CD3 and a second scFv specifically binds to/interacts with EpCAM.

It is further preferred that said at least one further antigen-interaction-site of the bispecific binding molecule of the invention is humanized.

In a further embodiment, the invention encompasses a nucleic acid sequence encoding an above defined bispecific binding molecule of the invention. Preferably, said nucleic acid sequence selected from the group consisting of:
(a) a nucleotide sequence encoding the mature form of a protein comprising the amino acid sequence selected from the group of SEQ ID Nos: 20, 34 or 36;
(b) a nucleotide sequence comprising or consisting of a DNA sequence selected from the group of SEQ ID NOs: 19, 33 or 35;
(c) a nucleotide sequence hybridizing with the complementary strand of a nucleotide sequence as defined in (b) under stringent hybridization conditions;
(d) a nucleotide sequence encoding a protein derived from the protein encoded by a nucleotide sequence of (a) or (b) by way of substitution, deletion and/or addition of one or several amino acids of the amino acid sequence encoded by the nucleotide sequence of (a) or (b);
(e) a nucleotide sequence encoding a protein having an amino acid sequence at least 60%, preferably 70%, more preferably 80%, particularly preferably 90%, even more preferably 95% and most preferably 99% identical to the amino acid sequence encoded by the nucleotide sequence of (a) or (b);
(f) a nucleotide sequence which is degenerate as a result of the genetic code to a nucleotide sequence of any one of (a) to (e).

The term "hybridizing" as used herein refers to polynucleotides which are capable of hybridizing to the complementary strand of the recited nucleic acid sequence or parts thereof or to the recited nucleic acid sequence or parts thereof. Therefore, said nucleic acid sequence may be useful as probes in Northern or Southern Blot analysis of RNA or DNA preparations, respectively, or can be used as oligonucleotide primers in PCR analysis dependent on their respective size. Preferably, said hybridizing polynucleotides comprise at least 10, more preferably at least 15 nucleotides while a hybridizing polynucleotide of the present invention to be used as a probe preferably comprises at least 100, more preferably at least 200, or most preferably at least 500 nucleotides.

It is well known in the art how to perform hybridization experiments with nucleic acid molecules, i.e. the person skilled in the art knows what hybridization conditions s/he has to use in accordance with the present invention. Such hybridization conditions are referred to in standard text books such as Sambrook et al. (loc cit.) and other standard laboratory manuals known by the person skilled in the art or as recited above. Preferred in accordance with the present inventions are polynucleotides which are capable of hybridizing to the polynucleotides of the invention or parts thereof, under stringent hybridization conditions.

"Stringent hybridization conditions" refer, i.e. to an overnight incubation at 42° C. in a solution comprising 50% formamide, 5×SSC (750 mM NaCl, 75 mM sodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C. Also contemplated are nucleic acid molecules that hybridize to the polynucleotides of the invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37° C. in a solution comprising 6×SSPE (20×SSPE=3M NaCl; 0.2M NaH2po4; 0.02M EDTA, pH 7.4), 0.5% SDS, 30% formamide, 100 µg/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC). It is of note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

The recited nucleic acid molecules may be, e.g., DNA, cDNA, RNA or synthetically produced DNA or RNA or a recombinantly produced chimeric nucleic acid molecule or mixtures of chimeras thereof comprising any of those polynucleotides either alone or in combination.

It is evident to the person skilled in the art that regulatory sequences may be added to the nucleic acid molecule of the invention. For example, promoters, transcriptional enhancers and/or sequences which allow for induced expression of the polynucleotide of the invention may be employed. A suitable inducible system is for example tetracycline-regulated gene expression as described, e.g., by Gossen and Bujard (Proc. Natl. Acad. Sci. USA 89 (1992), 5547-5551) and Gossen et al. (Trends Biotech. 12 (1994), 58-62), or a dexamethasone-inducible gene expression system as described, e.g. by Crook (1989) EMBO J. 8, 513-519.

Furthermore, it is envisaged for further purposes that nucleic acid molecules may contain, for example, thioester bonds and/or nucleotide analogues. Said modifications may be useful for the stabilization of the nucleic acid molecule against endo- and/or exonucleases in the cell. Said nucleic acid molecules may be transcribed by an appropriate vector containing a chimeric gene which allows for the transcription of said nucleic acid molecule in the cell. In this respect, it is also to be understood that such polynucleotide can be used for "gene targeting" or "gene therapeutic" approaches. In another embodiment said nucleic acid molecules are labeled. Methods for the detection of nucleic acids are well known in the art, e.g., Southern and Northern blotting, PCR or primer extension. This embodiment may be useful for screening methods for verifying successful introduction of the nucleic acid molecules described above during gene therapy approaches.

Said nucleic acid molecule(s) may be a recombinantly produced chimeric nucleic acid molecule comprising any of the aforementioned nucleic acid molecules either alone or in combination. Preferably, the nucleic acid molecule is part of a vector.

The present invention therefore also relates to a vector comprising the nucleic acid molecule of the present invention.

Many suitable vectors are known to those skilled in molecular biology, the choice of which would depend on the function desired and include plasmids, cosmids, viruses, bacteriophages and other vectors used conventionally in genetic engineering. Methods which are well known to those skilled in the art can be used to construct various plasmids and vectors; see, for example, the techniques described in Sambrook et al. (loc cit.) and Ausubel, Current Protocols in Molecular Biology, Green Publishing Associates and Wiley Interscience, N.Y. (1989), (1994). Alternatively, the polynucleotides and vectors of the invention can be reconstituted into liposomes for delivery to target cells. As discussed in further details below, a cloning vector was used to isolate individual sequences of DNA. Relevant sequences can be transferred into expression vectors where expression of a particular polypeptide is required. Typical cloning vectors include pBluescript SK, pGEM, pUC9, pBR322 and pGBT9. Typical expression vectors include PTRE, pCAL-n-EK, pESP-1, pOP13CAT.

Preferably said vector comprises a nucleic acid sequence which is a regulatory sequence operably linked to said nucleic acid sequence encoding a single chain antibody constructs defined herein.

Such regulatory sequences (control elements) are known to the artisan and may include a promoter, a splice cassette, translation initiation codon, translation and insertion site for introducing an insert into the vector. Preferably, said nucleic acid molecule is operatively linked to said expression control sequences allowing expression in eukaryotic or prokaryotic cells.

It is envisaged that said vector is an expression vector comprising the nucleic acid molecule encoding a bispecific binding molecule of the invention.

The term "regulatory sequence" refers to DNA sequences, which are necessary to effect the expression of coding sequences to which they are ligated. The nature of such control sequences differs depending upon the host organism. In prokaryotes, control sequences generally include promoter, ribosomal binding site, and terminators. In eukaryotes generally control sequences include promoters, terminators and, in some instances, enhancers, transactivators or transcription factors. The term "control sequence" is intended to include, at a minimum, all components the presence of which are necessary for expression, and may also include additional advantageous components.

The term "operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences. In case the control sequence is a promoter, it is obvious for a skilled person that double-stranded nucleic acid is preferably used.

Thus, the recited vector is preferably an expression vector. An "expression vector" is a construct that can be used to transform a selected host and provides for expression of a coding sequence in the selected host. Expression vectors can for instance be cloning vectors, binary vectors or integrating vectors. Expression comprises transcription of the nucleic acid molecule preferably into a translatable mRNA. Regulatory elements ensuring expression in prokaryotes and/or eukaryotic cells are well known to those skilled in the art. In the case of eukaryotic cells they comprise normally promoters ensuring initiation of transcription and optionally poly-A signals ensuring termination of transcription and stabilization of the transcript. Possible regulatory elements permitting expression in prokaryotic host cells comprise, e.g., the $P_L$, lac, trp or tac promoter in *E. coli* and examples of regulatory elements permitting expression in eukaryotic host cells are the AOX1 or GALL promoter in yeast or the CMV-, SV40-, RSV-promoter (Rous sarcoma virus), CMV-enhancer, SV40-enhancer or a globin intron in mammalian and other animal cells. Beside elements which are responsible for the initiation of transcription such regulatory elements may also comprise transcription termination signals, such as the SV40-poly-A site or the tk-poly-A site, downstream of the polynucleotide. Furthermore, depending on the expression system used leader sequences capable of directing the polypeptide to a cellular compartment or secreting it into the medium may be added to the coding sequence of the recited nucleic acid sequence and are well known in the art; see also, e.g., appended example 3. The leader sequence(s) is (are) assembled in appropriate phase with translation, initiation and termination sequences, and preferably, a leader sequence capable of directing secretion of translated protein, or a portion thereof, into the periplasmic space or extracellular medium. Optionally, the heterologous sequence can encode a fusion protein including an N-terminal identification peptide imparting desired characteristics, e.g., stabilization or simplified purification of expressed recombinant product; see supra. In this context, suitable expression vectors are known in the art such as Okayama-Berg cDNA expression vector pcDV1 (Pharmacia), pCDM8, pRc/CMV, pcDNA1, pcDNA3 (In-vitrogene), pEF-DHFR, pEF-ADA or pEF-neo (Mack et al. PNAS (1995) 92, 7021-7025 and Raum et al. Cancer Immunol Immunother (2001) 50(3), 141-150) or pSPORT1 (GIBCO BRL).

Preferably, the expression control sequences will be eukaryotic promoter systems in vectors capable of transforming of transfecting eukaryotic host cells, but control sequences for prokaryotic hosts may also be used. Once the vector has been incorporated into the appropriate host, the host is maintained under conditions suitable for high level expression of the nucleotide sequences, and as desired, the collection and purification of the bispecific binding molecule of the invention may follow; see, e.g., the appended examples.

An alternative expression system which could be used to express a cell cycle interacting protein is an insect system. In one such system, *Autographa californica* nuclear polyhedrosis virus (AcNPV) is used as a vector to express foreign genes in *Spodoptera frugiperda* cells or in *Trichoplusia larvae*. The coding sequence of a recited nucleic acid molecule may be cloned into a nonessential region of the virus, such as the polyhedrin gene, and placed under control of the polyhedrin promoter. Successful insertion of said coding sequence will render the polyhedrin gene inactive and produce recombinant virus lacking coat protein coat. The recombinant viruses are then used to infect *S. frugiperda* cells or *Trichoplusia larvae* in which the protein of the invention is expressed (Smith, J. Virol. 46 (1983), 584; Engelhard, Proc. Nat. Acad. Sci. USA 91 (1994), 3224-3227).

Additional regulatory elements may include transcriptional as well as translational enhancers. Advantageously, the above-described vectors of the invention comprises a selectable and/or scorable marker.

Selectable marker genes useful for the selection of transformed cells and, e.g., plant tissue and plants are well known to those skilled in the art and comprise, for example, antimetabolite resistance as the basis of selection for dhfr, which confers resistance to methotrexate (Reiss, Plant Physiol. (Life Sci. Adv.) 13 (1994), 143-149); npt, which confers resistance to the aminoglycosides neomycin, kanamycin and paromycin (Herrera-Estrella, EMBO J. 2 (1983), 987-995) and hygro, which confers resistance to hygromycin (Marsh, Gene 32 (1984), 481-485). Additional selectable genes have been described, namely trpB, which allows cells to utilize indole in place of tryptophan; hisD, which allows cells to utilize histinol in place of histidine (Hartman, Proc. Natl. Acad. Sci. USA 85 (1988), 8047); mannose-6-phosphate isomerase which allows cells to utilize mannose (WO 94/20627) and ODC (ornithine decarboxylase) which confers resistance to the ornithine decarboxylase inhibitor, 2-(difluoromethyl)-DL-ornithine, DFMO (McConlogue, 1987, In: Current Communications in Molecular Biology, Cold Spring Harbor Laboratory ed.) or deaminase from *Aspergillus terreus* which confers resistance to Blasticidin S (Tamura, Biosci. Biotechnol. Biochem. 59 (1995), 2336-2338).

Useful scorable markers are also known to those skilled in the art and are commercially available. Advantageously, said marker is a gene encoding luciferase (Giacomin, P I. Sci. 116 (1996), 59-72; Scikantha, J. Bact. 178 (1996), 121), green fluorescent protein (Gerdes, FEBS Lett. 389 (1996), 44-47) or β-glucuronidase (Jefferson, EMBO J. 6 (1987), 3901-3907). This embodiment is particularly useful for simple and rapid screening of cells, tissues and organisms containing a recited vector.

As described above, the recited nucleic acid molecule can be used alone or as part of a vector to express the bispecific binding molecule of the invention in cells, for, e.g., purification but also for gene therapy purposes. The nucleic acid molecules or vectors containing the DNA sequence(s) encoding any one of the above described bispecific binding molecule of the invention is introduced into the cells which in turn produce the polypeptide of interest. Gene therapy, which is based on introducing therapeutic genes into cells by ex-vivo or in-vivo techniques is one of the most important applications of gene transfer. Suitable vectors, methods or gene-delivery systems for in-vitro or in-vivo gene therapy are described in the literature and are known to the person skilled in the art; see, e.g., Giordano, Nature Medicine 2 (1996), 534-539; Schaper, Circ. Res. 79 (1996), 911-919; Anderson, Science 256 (1992), 808-813; Verma, Nature 389 (1994), 239; Isner, Lancet 348 (1996), 370-374; Muhlhauser, Circ. Res. 77 (1995), 1077-1086; Onodera, Blood 91 (1998), 30-36; Verma, Gene Ther. 5 (1998), 692-699; Nabel, Ann. N.Y. Acad. Sci. 811 (1997), 289-292; Verzeletti, Hum. Gene Ther. 9 (1998), 2243-51; Wang, Nature Medicine 2 (1996), 714-716; WO 94/29469; WO 97/00957, U.S. Pat. No. 5,580, 859; U.S. Pat. No. 5,589,466; or Schaper, Current Opinion in Biotechnology 7 (1996), 635-640. The recited nucleic acid molecules and vectors may be designed for direct introduction or for introduction via liposomes, or viral vectors (e.g., adenoviral, retroviral) into the cell. Preferably, said cell is a germ line cell, embryonic cell, or egg cell or derived therefrom, most preferably said cell is a stem cell. An example for an embryonic stem cell can be, inter alia, a stem cell as described in, Nagy, Proc. Natl. Acad. Sci. USA 90 (1993), 8424-8428.

The invention also provides for a host transformed or transfected with a vector of the invention. Said host may be produced by introducing said at least one of the above described vector of the invention or at least one of the above described nucleic acid molecules of the invention into the host. The presence of said at least one vector or at least one nucleic acid molecule in the host may mediate the expression of a gene encoding the above described single chain antibody constructs.

The described nucleic acid molecule or vector of the invention which is introduced in the host may either integrate into the genome of the host or it may be maintained extrachromosomally.

The host can be any prokaryote or eukaryotic cell.

The term "prokaryote" is meant to include all bacteria which can be transformed or transfected with DNA or RNA molecules for the expression of a protein of the invention. Prokaryotic hosts may include gram negative as well as gram positive bacteria such as, for example, *E. coli, S. typhimurium, Serratia marcescens* and *Bacillus subtilis*. The term "eukaryotic" is meant to include yeast, higher plant, insect and preferably mammalian cells. Depending upon the host employed in a recombinant production procedure, the protein encoded by the polynucleotide of the present invention may be glycosylated or may be non-glycosylated. Especially preferred is the use of a plasmid or a virus containing the coding sequence of the polypeptide of the invention and genetically fused thereto an N-terminal FLAG-tag and/or C-terminal His-tag. Preferably, the length of said FLAG-tag is about 4 to 8 amino acids, most preferably 8 amino acids. An above described polynucleotide can be used to transform or transfect the host using any of the techniques commonly known to those of ordinary skill in the art. Furthermore, methods for preparing fused, operably linked genes and expressing them in, e.g., mammalian cells and bacteria are well-known in the art (Sambrook, loc cit.).

Preferably, said the host is a bacterium or an insect, fungal, plant or animal cell.

It is particularly envisaged that the recited host may be a mammalian cell. Particularly preferred host cells comprise CHO cells, COS cells, myeloma cell lines like SP2/0 or NS/0. As illustrated in the appended examples, particularly preferred are CHO-cells as hosts.

More preferably said host cell is a human cell or human cell line, e.g. per.c6 (Kroos, Biotechnol. Prog., 2003, 19:163-168).

In a further embodiment, the present invention thus relates to a process for the production of bispecific binding molecule of the invention comprising cultivating a cell and/or the host of the invention under conditions suitable for the expression/ allowing the expression of bispecific binding molecule and isolating/recovering the bispecific binding molecule from the cell or the culture/culture medium.

The transformed hosts can be grown in fermentors and cultured according to techniques known in the art to achieve optimal cell growth. The polypeptide of the invention can then be isolated from the growth medium, cellular lysates, or cellular membrane fractions. The isolation and purification of the, e.g., microbially expressed polypeptides of the invention may be by any conventional means such as, for example, preparative chromatographic separations and immunological separations such as those involving the use of monoclonal or polyclonal antibodies directed, e.g., against a tag of the polypeptide of the invention or as described in the appended examples.

The conditions for the culturing of a host which allow the expression are known in the art to depend on the host system and the expression system/vector used in such process. The parameters to be modified in order to achieve conditions allowing the expression of a recombinant polypeptide are known in the art. Thus, suitable conditions can be determined by the person skilled in the art in the absence of further inventive input.

Once expressed, the bispecific binding molecule of the invention can be purified according to standard procedures of the art, including ammonium sulfate precipitation, affinity columns, column chromatography, gel electrophoresis and the like; see, Scopes, "Protein Purification", Springer-Verlag, N.Y. (1982). Substantially pure polypeptides of at least about 90 to 95% homogeneity are preferred, and 98 to 99% or more homogeneity are most preferred, for pharmaceutical uses. Once purified, partially or to homogeneity as desired, the bispecific binding molecule of the invention may then be used therapeutically (including extracorporeally) or in developing and performing assay procedures. Furthermore, examples for methods for the recovery of the bispecific binding molecule of the invention from a culture are described in detail in the appended examples.

Furthermore, the invention provides for a composition comprising a bispecific binding molecule of the invention or a bispecific binding molecule as produced by the process disclosed above, a nucleic acid molecule of the invention, a vector or a host of the invention. Said composition may, optionally, also comprise a proteinaceous compound capable of providing an activation signal for immune effector cells. Most preferably, said composition is a pharmaceutical composition further comprising, optionally, suitable formulations of carrier, stabilizers and/or excipients.

In the light of the present invention, said "proteinaceous compounds" providing an activation signal for immune effector cells" may be, e.g. an activation signal for T cells. Preferred formats of proteinaceous compounds comprise bispecific antibodies and fragments or derivatives thereof, e.g. bispecific scFv. Preferably, said activation signal for T cells may be provided via the T cell receptor (TCR), more preferably via CD3 molecule of the TCR. Proteinaceous compounds can comprise, but are not limited to, scFv's specific for CD3, scFv's specific for the T cell receptor or superantigens. Superantigens directly bind to certain subfamilies of T cell receptor variable regions in an MHC-independent manner thus mediating the primary T cell activation signal. The proteinaceous compound may also provide an activation signal for an immune effector cell which is a non-T cell. Examples of immune effector cells which are non-T cells comprise, inter alia, B cells and NK cells.

In accordance with this invention, the term "pharmaceutical composition" relates to a composition for administration to a patient, preferably a human patient. In a preferred embodiment, the pharmaceutical composition comprises a composition for parenteral, transdermal, intraluminal, intra arterial, intrathecal administration or by direct injection into the tissue or tumour. It is in particular envisaged that said pharmaceutical composition is administered to a patient via infusion or injection. Administration of the suitable compositions may be effected by different ways, e.g., by intravenous, intraperitoneal, subcutaneous, intramuscular, topical or intradermal administration. The pharmaceutical composition of the present invention may further comprise a pharmaceutically acceptable carrier. Examples of suitable pharmaceutical carriers are well known in the art and include phosphate buffered saline solutions, water, emulsions, such as oil/water emulsions, various types of wetting agents, sterile solutions, etc. Compositions comprising such carriers can be formulated by well known conventional methods. These pharmaceutical compositions can be administered to the subject at a suitable dose. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Generally, the regimen as a regular administration of the pharmaceutical composition should be in the range of 1 µg to 5 g units per day. However, a more preferred dosage for continuous infusion might be in the range of 0.01 µg to 2 mg, preferably 0.01 µg to 1 mg, more preferably 0.01 µg to 100 µg, even more preferably 0.01 µg to 50 µg and most preferably 0.01 µg to 10 µg units per kilogram of body weight per hour. Particularly preferred dosages are recited herein below. Progress can be monitored by periodic assessment. Dosages will vary but a preferred dosage for intravenous administration of DNA is from approximately $10^6$ to $10^{12}$ copies of the DNA molecule. The compositions of the invention may be administered locally or systematically. Administration will generally be parenterally, e.g., intravenously; DNA may also be administered directed to the target site, e.g., by biolistic delivery to an internal or external target site or by catheter to a site in an artery. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishes, electrolyte replenishers (such as those based on Ringer's dextrose), and the like. Preservatives and other additives may also be present such as, for example, antimicrobials, anti-oxidants, chelating agents, and inert gases and the like. In addition, the pharmaceutical composition of the present invention might comprise proteinaceous carriers, like, e.g., serum albumine or immunoglobuline, preferably of human origin. It is envisaged that the pharmaceutical composition of the invention might comprise, in addition to the proteinaceous CD3 binding molecules or nucleic acid molecules or vectors encoding the same (as described in this invention), further biologically active agents, depending on the intended use of the pharmaceutical composition. Such agents might be drugs acting on the gastrointestinal system, drugs acting as cytostatica, drugs preventing hyperurikemia, drugs inhibiting immunereactions (e.g. corticosteroids), drugs acting on the circulatory system and/or agents such as T-cell co-stimulatory molecules or cytokines known in the art.

Possible indications for administration of the composition(s) of the invention are tumorous diseases, cancers, especially epithelial cancers/carcinomas such as breast cancer, colon cancer, prostate cancer, head and neck cancer, non-melanotic skin cancer, cancers of the genito-urinary tract, e.g. ovarial cancer, endometrial cancer, cervix cancer and kidney cancer, lung cancer, gastric cancer, cancer of the small intestine, liver cancer, pancreas cancer, gall bladder cancer, cancers of the bile duct, esophagus cancer, cancer of the salivatory glands and cancer of the thyroid gland or other tumorous diseases like haematological tumors, melanomas, gliomas, sarcomas, e.g. osteosarcomas. Further indications for administration of the composition(s) of the invention are proliferative diseases, an inflammatory diseases, an immunological disorders, an autoimmune diseases, an infectious diseases, viral diseases, allergic reactions, parasitic reactions, graft-versus-host diseases or host-versus-graft diseases.

The composition of the invention as described above may also be a diagnostic composition further comprising, optionally, means and methods for detection of proliferative diseases, tumorous diseases, inflammatory diseases, immunological disorders, autoimmune diseases, infectious diseases, viral diseases, allergic reactions, parasitic reactions, graft-versus-host diseases or host-versus-graft diseases.

The bispecific specific binding molecules of the invention are also suited for use in immunoassays in which they can be utilized in liquid phase or bound to a solid phase carrier. Examples of immunoassays which can utilize the polypeptide of the invention e.g. for diagnostic purposes are competitive and non-competitive immunoassays in either a direct or indirect format. Examples of such immunoassays are the enzyme linked immunosorbent assa (ELISA), enzyme immunoassay (EIA), radioimmunoassay (RIA), the sandwich (immunometric assay), dot blot and the Western blot assay. Further assays, which can be used for detecting the bispecific binding molecules e.g. in diagnostic assays are FACS-based assays, cytotoxic assays ($Cr^{51}$, fluorescence release) or dye release assays.

The bispecific specific binding molecules of the invention can be bound to many different carriers and used to isolate cells specifically bound to said polypeptides. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble, e.g. as beads, for the purposes of the invention.

Said diagnostic composition may be shipped in one or more container comprising, optionally (a) buffer(s), storage solutions and/or remaining reagents or materials required for the conduct of medical or scientific purposes. Furthermore, parts of the diagnostic composition of the invention can be packaged individually in vials or bottles or in combination in containers or multicontainer units.

There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds.

In a most preferred embodiment of the present invention, the use of a bispecific binding molecule of the invention or a binding molecule produced by a process of the invention, of a vector or of a host of the invention for the preparation of a pharmaceutical composition is envisaged. Said pharmaceutical composition may be employed in the prevention, treatment or amelioration of a proliferative disease, a tumorous disease, an inflammatory disease, an immunological disorder, an autoimmune disease, an infectious disease, viral disease, allergic reactions, parasitic reactions, graft-versus-host diseases or host-versus-graft diseases.

The invention also relates to a method for the prevention, treatment or amelioration of a proliferative disease, a tumorous disease, an inflammatory disease, an immunological disorder, an autoimmune disease, an infectious disease, viral disease, allergic reactions, parasitic reactions, graft-versus-host diseases or host-versus-graft diseases comprising the administrating an effective amount of a bispecific binding molecule of the invention or a binding molecule produced by a process of the invention, of a vector or of a host of the invention to a subject in need of such a prevention, treatment or amelioration. Preferably, said subject is a human. It is further envisaged, that the method of treatment further comprises the administration of an effective amount of a proteinaceous compound capable of providing an activation signal for immune effector cells. Preferably, said proteinaceous compound is administered simultaneously or non-simultaneously with a bispecific binding molecule of the invention or as produced by the process of the invention, a nucleic acid molecule, a vector or a host of the invention.

Finally, the invention provides for a kit comprising the bispecific binding molecule of the invention or as produced by the process of the invention, a nucleic acid molecule, a vector or a host of the invention.

Said kit is particularly useful in the preparation of the pharmaceutical composition of the present invention and may, inter alia, consist of a container useful for injections or infusions. Advantageously, the kit of the present invention further comprises, optionally (a) buffer(s), storage solutions and/or remaining reagents or materials required for the conduct of medical or scientific purposes. Furthermore, parts of the kit of the invention can be packaged individually in vials or bottles or in combination in containers or multicontainer units. The kit of the present invention may be advantageously used, inter alia, for carrying out the method of the invention and could be employed in a variety of applications referred herein, e.g., as a research tools or medical tools. The manufacture of the kits preferably follows standard procedures which are known to the person skilled in the art.

These and other embodiments are disclosed and encompassed by the description and Examples of the present invention. Further literature concerning any one of the antibodies, methods, uses and compounds to be employed in accordance with the present invention may be retrieved from public libraries and databases, using for example electronic devices. For example, the public database "Medline", available on the Internet, may be utilized, for example under www.ncbi.nlm-.nih.gov/PubMed/medline.html. Further databases and addresses, such as www.ncbi.nlm.nih.gov/, www.infobiogen.fr/, www.fmi.ch/biology/researchtools.html, www-.tiqr.orq/, are known to the person skilled in the art and can also be obtained using, e.g., http://www.lycos.com or www-.google.com.

The figures show:

FIG. 1.

A) The nucleotide and amino acid sequence of the humanized anti-CD3 antibody light chain and heavy chain (SEQ ID NOs.:9-12); B) the nucleotide and amino acid sequence of the bispecific anti-CD19xhum.anti-CD3 antibody (SEQ ID NO.: 19, 20); C) the nucleotide and amino acid sequence of the bispecific anti-EpCAM (5-10) xhum. anti-CD3 antibody (SEQ ID NO.:35, 36); D) the nucleotide and amino acid sequence of the bispecific anti-EpCAM (3-1)xhum. anti-CD3 antibody (SEQ ID NO.:33, 34),

FIG. 2.

FACS analysis of the binding affinity of different constructs to CD3 and CD19 or EpCAM.

FACS analysis of CD3 binding was performed with CD3 positive Jurkat cells. A) Bispecific anti-CD19x hum. anti-CD3 antibody construct (SEQ ID NO.: 20). Binding to CD19 was shown with CD19 positive Nalm6 cells.; B) Bispecific anti-EpCAM (3-1)x hum. anti-CD3 antibody construct (SEQ ID NO.: 34). Binding to EpCAM was shown with EpCAM positive KatoIII cells.; C) Bispecific anti-EpCAM (5-10)x hum. anti-CD3 antibody construct (SEQ ID NO.: 36). Binding to EpCAM was shown with EpCAM positive KatoIII cells. A shift to the right shows binding.

FIG. 3:

Elution pattern of bispecific anti-CD19x hum. anti-CD3 antibody containing protein fractions from a Zn-Chelating FRACTOGEL® column.

High adsorption at 280 nm from 50-530 ml retention time was due to non-bound protein in the column flow-through. The arrow at the peak at 617.44 ml indicates the humanized bispecific construct containing protein fraction that was used or further purified.

FIG. 4:

Protein elution pattern from a SEPHADEX S200® gel filtration column.

The protein peak at 82.42 ml containing bispecific antibody against anti-CD19xhum. anti-CD3 corresponds to a molecular weight of ca. 52 kD. Fractions were collected from 40-120 ml retention time.

FIG. 5:

A) SDS-PAGE analysis of bispecific anti-CD19x hum. anti-CD3 antibody protein fractions. Lane M: Molecular weight marker, Lane 1: cell culture supernatant; lane 2: IMAC eluate; lane 3: gel filtration aggregate peak; lane 4: purified bispecific antibody anti-CD19x hum. anti-CD3;

B) Western blot analysis of purified bispecific anti-CD19xhum. anti-CD3 antibody Lane M: Molecular weight marker, Lane 1: cell culture supernatant; lane 2: IMAC eluate; lane 3: gel filtration aggregate peak; lane 4: purified bispecific antibody anti-CD19 xhum. anti-CD3 obtained from gel filtration.

FIG. 6

Cytotoxicity assay of bispecific anti-CD19x hum. anti-CD3 antibody (SEQ ID NO.: 20).

NALM-6 cells were used as target cells and CD4 positive CB15 T-cells as effector cells in a E:T ratio of 1:10.

The invention will now be described by reference to the following biological examples which are merely illustrative and are not to be construed as a limitation of scope of the present invention.

EXAMPLE 1

Generation of Humanized Antibody Specific for the CD3 Antigen

The location of the CDRs of the CD3 specific antibody OKT3 was determined with reference to Kabat, E A, et al. Sequences of Proteins of Immunological Interest. 5th edition. 3 vols. Bethesda, Md.: National Institutes of Health. National Center for Biotechnology Information, 1991; 2597. NIH publication no. 91-3242.

The human framework regions chosen to receive the transplanted CDRs were KOL and REI for the heavy and light chains respectively. The structures of these proteins have been solved crystallographically (REI: Palm (1975) Hoppe Seylers Z Physiol Chem 356, 167-191, KOL: Schmidt (1983) Hoppe Seylers Z Physiol Chem 364, 713-747.)

A number of additional, murine residues were introduced into the human variable region frameworks according to Adair 1994 Hum. Antibod. Hybridomas, 5:41-48. These residues that have been changed are important for retaining original antigen specificity. Additional mutations were introduced in the CDR1, CDR2 and CDR3 of the light chain. The CDR sequences of the humanized OKT and improved humanized CD3 of the invention are shown in Table 2. The sequence of the improved humanized CD3 binding molecule is shown in FIG. 1A; SEQ ID No.9-12.

TABLE 2

The CDRs of the light chain of the CD3 specific antibody OKT3.

| CDRs of anti-CD3 | Amino acid sequence of humanized OKT3 | Amino acid sequence of humanized CD3 |
| --- | --- | --- |
| L1 | SASSSVSYMN (SEQ ID NO: 38) | RASSSVSYMN (SEQ ID No.: 4) |
| L2 | DTSKLAS (SEQ ID NO: 39) | DTSKVAS (SEQ ID No.: 6) |
| L3 | QQWSSNPFT (SEQ ID NO: 40) | QQWSSNPLT (SEQ ID No.: 8) |

EXAMPLE 2

Construction of a Bispecific Single Chain Antibody with Humanized Anti-CD3 Part

EXAMPLE 2.1

Construction of Bispecific Single-Chain Anti-CD19xanti-CD3 Antibodies with Humanized Anti-CD3 Part The DNA encoding the scFv of the resulting humanized antibody was obtained by gene synthesis and further subjected to genetic fusion with a CD19-specific scFv to obtain a bispecific single chain antibody (FIG. 1B, SEQ ID NO.:19, 20). The bispecific single chain antibody was subcloned with the restriction enzymes EcoRI and SalI into the mammalian expression vector pEF-DHFR.

EXAMPLE 2.2

Construction of Bispecific Single-Chain Anti-EpCAMxanti-CD3 Antibodies with Humanized Anti-CD3 Part In addition to the bispecific constructs described in Example 1.1 two further bispecific single chain antibodies with different tumor specificities were constructed. The CD19 specificity of the bispecific anti-CD19xhum. anti-CD3 was replaced by two selected EpCAM antibodies 5-10 and 3-1. Thus, two EpCAM-specific bispecific single chain antibody constructs anti-EpCAM(5-10)xhum. anti-CD3 (SEQ ID NO.:35, 36) and anti-EpCAM (3-1)xhum. anti-CD3 (SEQ ID NO.:33, 34) were obtained.

EXAMPLE 3

Expression of the Bispecific Single Chain Antibodies with Humanized Anti-CD3 Part The anti-CD19xhum. anti-CD3 and anti-EpCAMxhum. anti-CD3 constructs (SEQ ID 19, 20, 33, 34, 35, 36) were expressed by stable transfection into DHFR deficient Chinese hamster ovary (CHO) cells as described by Mack, M. et al. (1995) Proc Natl Acad Sci USA 92, 7021-7025. Transfection of the expression vector was performed after calcium phosphate treatment of the cells (Sambrook et. al. 1989).

EXAMPLE 4

FACS Analysis of Binding Activity of the Single Chain Bispecific Antibodies with Humanized Anti-CD3 Part In order to test the functionality with regard to binding capability a FACS analysis was performed.

EXAMPLE 4.1

Flow Cytometric Binding Analysis of Anti-CD19xhum. Anti-CD3 Bispecific Antibody CD19 positive Nalm 6 cells (human B cell precursor leukaemia) and CD3 positive Jurkat cells (human T cell leukemia) were used. 200,000 Nalm 6 cells and 200,000 Jurkat cells were incubated with 50 µl the pure cell culture supernatant of CHO cells transfected with the anti-CD19xhum. anti-CD3 specific polypeptide for 30 min on ice. The cells were washed twice in PBS. Then the binding of the construct was detected via its C-terminal Histidin Tag with a murine Penta H is antibody (diluted 1:20 in 50 µl PBS with 2% FCS; Qiagen) followed by a washing step and a Phycoerythrin conjugated Fc gamma specific antibody (Dianova), diluted 1:100 in 50 µl PBS with 2% FCS (FIG. 2A, thick line). As negative control fresh cell culture medium instead of cell culture supernatant was used (FIG. 2, thin line).

Cells were analysed by flow cytometry on a FACS-Calibur (Becton Dickinson, Heidelberg). FACS staining and measuring of the fluorescence intensity were performed as described in Current Protocols in Immunology (Coligan, Kruisbeek, Margulies, Shevach and Strober, Wiley-Interscience, 2002). The binding activity of the bispecific binding molecule was compared to the binding activity of the corresponding control bispecific antibody with the humanized OKT3 part as described in prior art.

As shown in FIG. 2, both anti-CD19 xhum. OKT3 and anti-CD19xhum. anti-CD3 (improved hum. OKT3) bound well CD19 and CD3.

EXAMPLE 4.2

Figure 2B:
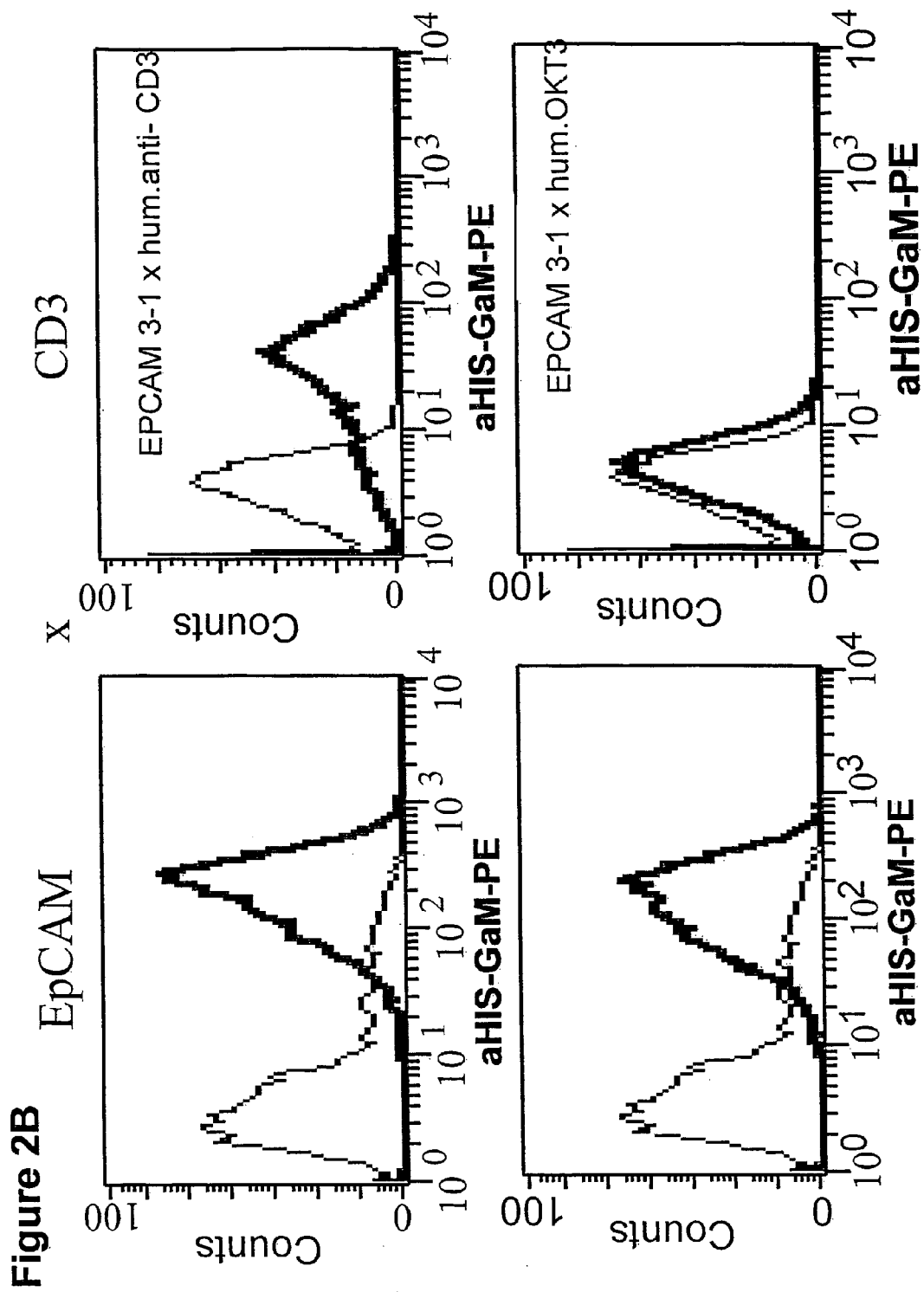
Figure 2C:
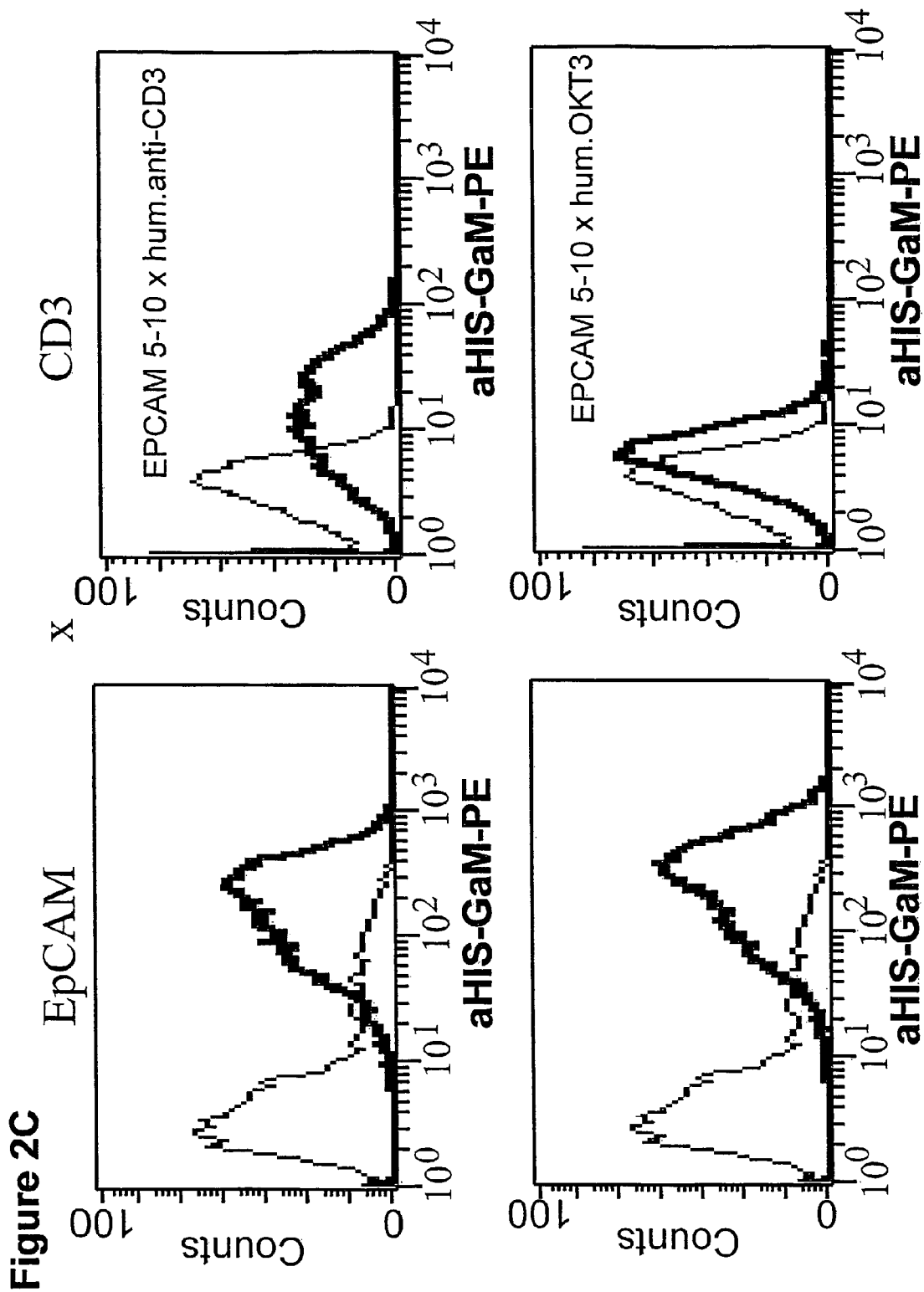

Flow Cytometric Binding Analysis of Anti-EpCAMxhum. Anti-CD3 Bispecific Antibody For testing of the binding abilities of the EpCAM specific bispecific antibodies the assay as described in Example 4.1 was repeated with following modifications: instead of Nalm 6 cells EpCAM positive Kato III cells were used (stomach carcinoma cell line; ATCC HTB-103) and the supernatants of the CHO cells transfected with the EpCAM bispecific antibodies were applied. The results of the EpCAM binding assays are shown in FIGS. 2B and 2C. A corresponding bispecific antibody with a humanized OKT3 as described in the prior art was used as a control.

As shown in FIGS. 2B and 2C, the bispecific construct comprising the humanized anti-CD3 (SEQ ID Nos. 34, 36) of the invention show much better binding than the constructs with humanized OKT3.

EXAMPLE 5

Purification of the Bispecific Constructs with the Improved Humanized Anti-CD3 Part In order to purify the bispecific single chain constructs anti-CD19xhum. anti-CD3 stably transfected CHO cells were grown in roller bottles with HiClone® CHO modified DMEM medium (HiQ) for 7 days before harvest. The cells were removed by centrifugation and the supernatant, containing the expressed protein was stored at −20° C.

Äkta FPLC System® (Pharmacia) and Unicorn Software were used for chromatography. All chemicals were of research grade and purchased from Sigma (Deisenhofen, Germany) or Merck (Darmstadt, Germany).

The humanized bispecific single chain construct proteins were isolated in a two step purification process including immobilized metal affinity chromatography (IMAC) and gelfiltration.

Figure 3:
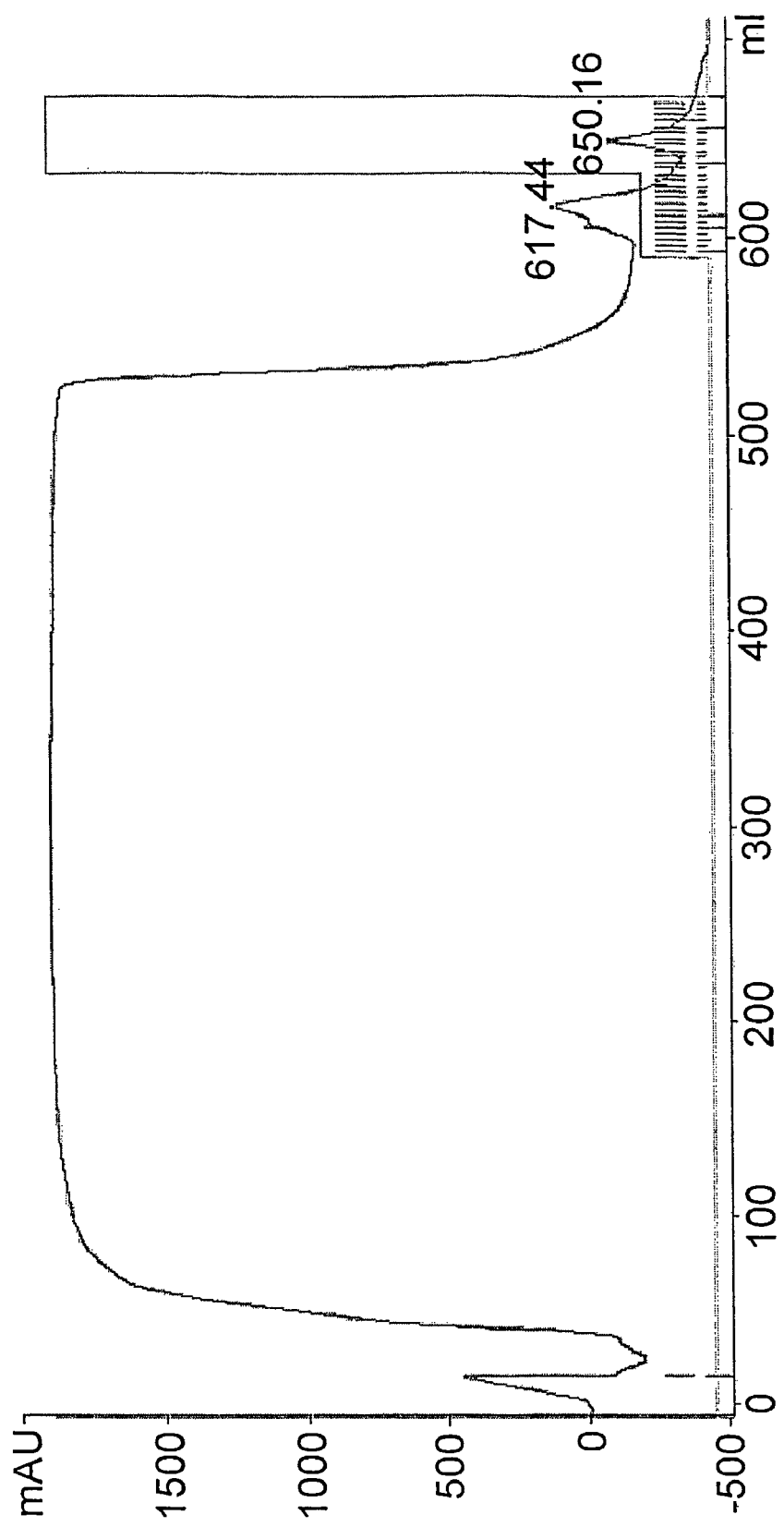

IMAC (immobilized metal affinity chromatography) was performed, using a Fractogel Column® (Pharmacia) that was loaded with $ZnCl_2$ according to the manufacturers protocol. The column was equilibrated with buffer A2 (20 mM sodium phosphate pH 7.5, 0.4 M NaCl) and the cell culture supernatant (500 ml) was applied to the column (10 ml) with a flow rate of 3 ml/min. The column was washed with buffer A2 to remove unbound sample. Bound protein was eluted using a 2-step gradient of buffer B2 (20 mM sodium phosphate pH 7.5, 0.4 M NaCl, 0.5 M Imidazol) Step 1: 20% buffer B2 in 10 column volumes; Step 2: 100% buffer B2 in 10 column volumes. Eluted protein fractions from the 100% step were pooled for further purification. (FIG. 3)

Figure 4:
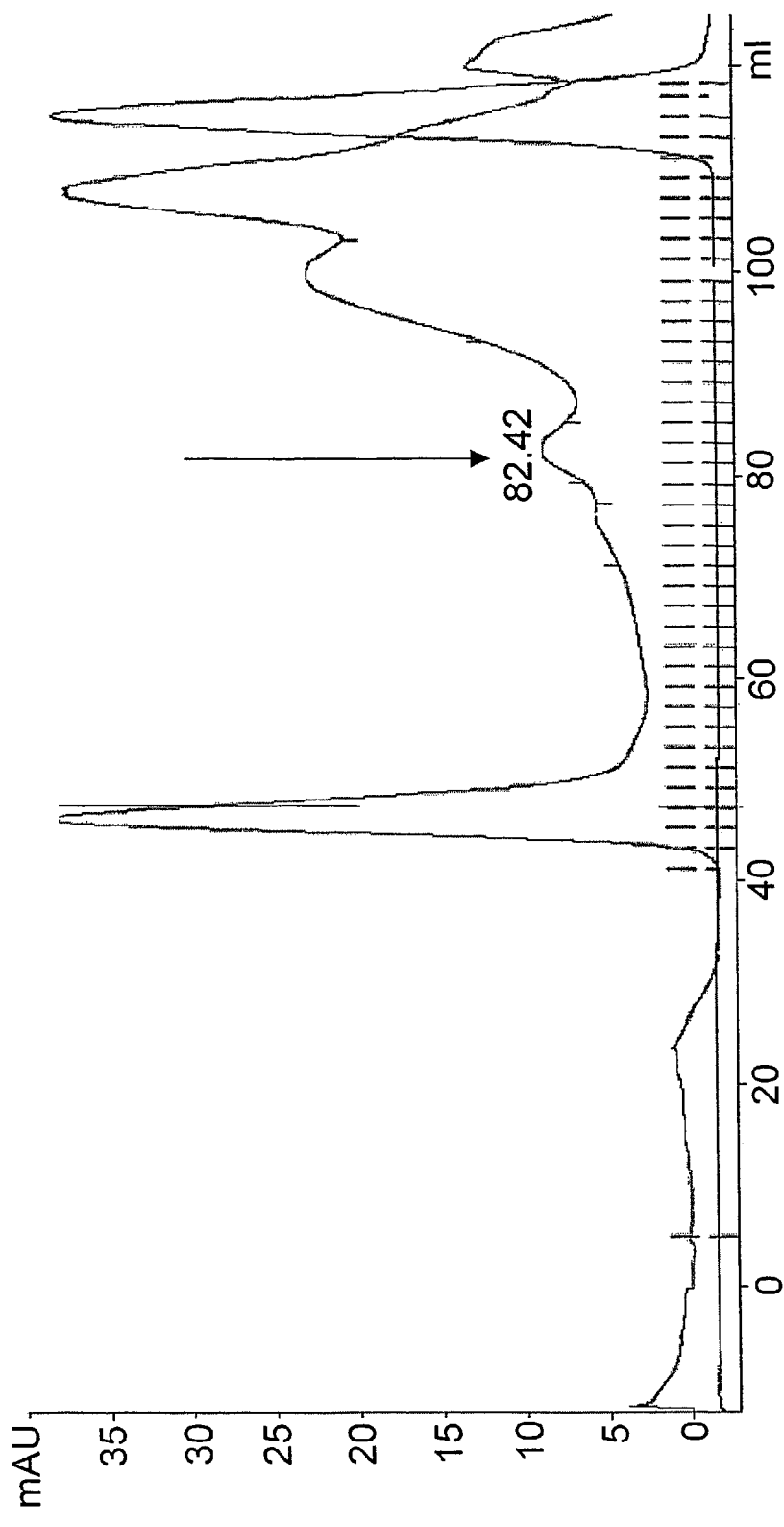

Gelfiltration chromatography was performed on a Sephadex S200 HiPrep Column® (Pharmacia) equilibrated with PBS (Gibco). Eluted protein samples (flow rate 1 ml/min) were subjected to SDS-PAGE and Western Blot for detection. The column was previously calibrated for molecular weight determination (molecular weight marker kit, Sigma MW GF-200). (FIG. 4)

Protein concentrations of the purified constructs were determined using protein assay dye (Micro BCA, Pierce) and IgG (Biorad) as standard protein. The yields of the protein are shown in Table 2. All constructs could be purified from cell culture supernatants. Comparable yields of purified protein were obtained for anti-CD19xhum. anti-CD3 (16/g/ml) and anti-CD19xhum. OKT3 (13.6 µg/ml).

The purified product had a molecular weight of 52 kDa under native conditions as determined by gelfiltration in PBS.

SDS-PAGE of the purified bispecific protein was performed on precast 4-12% Bis Tris gels (Invitrogen). Sample preparation and application were according to the manufacturers protocol. The molecular weight was determined with MultiMark Protein Standard® (Invitrogen). The gel was stained with colloidal Coomassie (Invitrogen protocol) showing a band at 52 kDa. The purity of the isolated protein was shown to be >95%.

Figure 5:
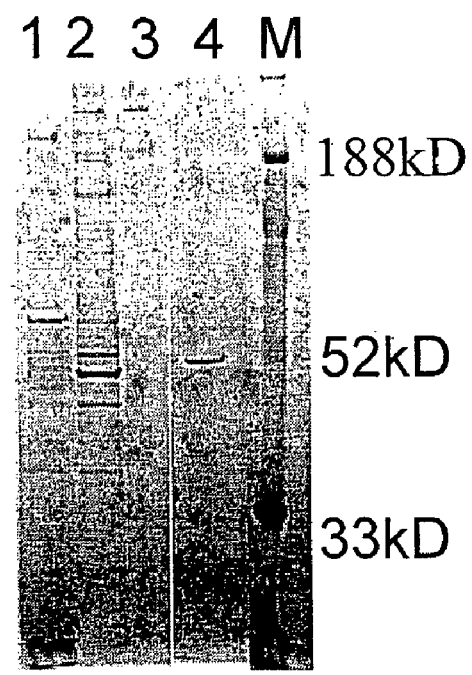
Figure 5:
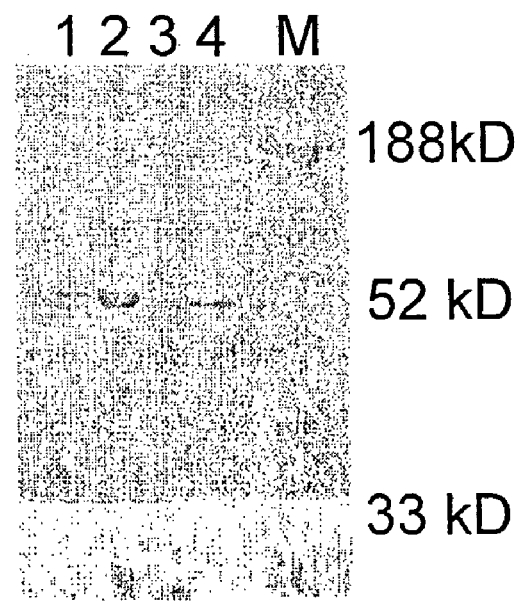

Western Blot was performed with an Optitran BA-S83 Membrane® and the Invitrogen Blot Module® according to the manufacturers protocol. The antibodies used were Penta His (Quiagen) and goat-anti-mouse-alkaline phosphatase (AP) (Sigma), the staining solution was BCIP/NBT (Sigma). The humanized bispecific protein was detected by Western Blot showing a 52 kD band (FIG. 5B). corresponding to the purified bispecific protein in the Coomassie stained SDS-gel (FIG. 5A).

EXAMPLE 6

Bioactivity of Bispecific Antibodies with Humanized Anti-CD3 Part

In order to certify the high cytotoxic activity of the constructed bispecific antibodies the following assays were performed.

EXAMPLE 6.1

Anti-CD19x hum. Anti-CD3 Bispecific Antibody (SEQ ID NO.: 20)

Target NALM-6 cells ($1.5 \times 10^7$) were labeled with 10 µM calcein AM (Molecular Probes) for 30 min at 37° C. in cell culture medium. After two washes in cell culture medium, cells were counted and mixed with CD4-positive CB15 T-cells. The resulting effector target cell mixture contained $2 \times 10^5$ Nalm6 cells and $2 \times 10^6$ CB15 cells per ml (E:T ratio of 1:10). Antibodies were diluted in RPMI/10% FCS to the required concentration. 50 µl of this solution was added to the cell suspension and incubated at 37° C./5% $CO_2$ for 2 hours. After the cytotoxic reaction, the released dye in the incubation medium was quantitated in a fluorescence reader and compared with the fluorescence signal from a control reaction where the cytotoxic compound was absent (negative control), and a reaction where the fluorescence signal was determined for totally lysed cells (for 10 min in 1% saponin) as positive control. On the basis of these readings, the specific cytotoxicity was calculated according to the following formula: [Fluorescence (Sample)−Fluorescence (Control)]: [Fluorescence (Total Lysis)−Fluorescence (Control)]×100.

Sigmoidal dose response curves typically had R2 values >0.97 as determined by Prism Software (GraphPad Software Inc., San Diego, USA). EC50 values calculated by the analysis program were used for comparison of bioactivity. The cytotoxicity of the bispecific antibody against CD19 and CD3 with humanized CD3 part is shown in FIG. 6. A corresponding bispecific antibody with a humanized OKT3 as described in the prior art was used as a control.

In the bispecific format the bispecific humanized improved CD3 (hum. anti-CD3) (SEQ ID NO. 20) has clearly increased cytotoxic activity (EC50 value 50 pg/ml) compared to the humanized OKT3 as described in Adair (EC50 value 195 pg/ml). Thus, these results demonstrate the major advantage of the improved humanized antibody binding to CD3 of the invention. Due to the about four-fold increase in cytotoxic activity of the improved humanized CD3 in the bispecific format this molecule is highly advantageous for therapeutic applications. Based on the stronger cytotoxic activity lower amounts of protein are required for therapy than of the prior art molecules. Thus, the bispecific molecules of the invention provide an important advantage over the prior art antibodies when treating patients since they show at the same time a high cytotoxic activity and are less immunogenic due to humanization. They therefore offer a clear improvement in the medical field.

What is claimed is:

1. A bispecific single chain antibody construct, whereby said bispecific single chain antibody construct comprises at least two domains,
   (a) wherein a first domain of said at least two domains specifically binds to the human CD3 complex, wherein said first domain comprises an amino acid sequence of an antibody light chain having the amino acid sequence selected from the group consisting of:
      (i) the amino acid sequence of SEQ ID NO.: 10;
      (ii) the amino acid sequence encoded by the nucleic acid sequence of SEQ ID NO.: 9; and
      (iii) the amino acid sequence encoded by a nucleic acid sequence
   which is degenerate as a result of the genetic code to the nucleic acid sequence of (ii); and
   (b) wherein a second domain is or contains at least one antigen-binding-site and/or at least one effector domain.

2. The bispecific single chain antibody construct according to claim 1, wherein the first domain which binds to the human CD3 complex is a scFv.

3. The bispecific single chain antibody construct according to claim 1, wherein the first domain which binds to the human CD3 complex comprises or consists of the amino acid sequence as depicted in SEQ ID NO.: 14 or encoded by the nucleic acid sequence of SEQ ID NO: 13.

4. The bispecific single chain antibody construct according to claim 1, wherein said antigen-binding-site in said second domain is specific for one or more cell surface molecule(s).

5. The bispecific single chain antibody construct according to claim 4, wherein said one or more cell surface molecule(s) is/are a tumor specific molecule(s).

6. The bispecific single chain antibody construct according to claim 4, wherein said second domain is a scFv.

7. The bispecific single chain antibody construct according to claim 4, wherein said second domain specifically binds to an antigen selected from the group consisting of EpCAM, CCR5, CD19, HER-2, HER-3, HER-4, EGFR, PSMA, CEA, MUC-1 (mucin), MUC2, MUC3, MUC4, MUC5AC, MUC5B, MUC7, bhCG, Lewis-Y, CD20, CD33, CD30, ganglioside GD3, 9-O-Acetyl-GD3, GM2, Globo H, fucosyl GM1, Poly SA, GD2, Carboanhydrase IX (MN/CA IX), CD44v6, Sonic Hedgehog (Shh), Wue-1, Plasma Cell Antigen, (membrane-bound) IgE, Melanoma Chondroitin Sulfate Proteoglycan (MCSP), CCR8, TNF-alpha precursor, STEAP, mesothelin, A33 Antigen, Prostate Stem Cell Antigen (PSCA), Ly-6 desmoglein 4, E-cadherin neoepitope, Fetal Acetylcholine Receptor, CD25, CA19-9 marker, CA-125 marker and Muellerian Inhibitory Substance (MIS) Receptor type II, sTn (sialylated Tn antigen; TAG-72), FAP (fibroblast activation antigen), endosialin, EGFRvIII, L6, SAS, CD63, TF-antigen, Cora antigen, CD7, CD22, Igα, Igβ, gp100, MT-MMPs, F19-antigen and CO-29.

8. The bispecific single chain antibody construct according to claim 7, wherein said second domain comprises an amino acid sequence selected from the group consisting of:
   (a) an amino acid sequence of SEQ ID NO.: 16 or 18;
   (b) an amino acid sequence encoded by the nucleic acid sequence of SEQ ID NO: 15 or 17; and (c) an amino acid sequence encoded by a nucleic acid sequence which is degenerate as a result of the genetic code to the nucleic acid sequence of any of (b).

9. The bispecific single chain antibody construct according to claim 8, wherein said single chain antibody construct comprises an amino acid sequence selected from the group consisting of:
   (a) an amino acid sequence of SEQ ID NO.: 20;
   (b) an amino acid sequence encoded by the nucleic acid sequence of SEQ ID NO.: 21; and
   (c) an amino acid sequence encoded by a nucleic acid sequence which is degenerate as a result of the genetic code to the nucleic acid sequence of (b).

10. The bispecific single chain antibody construct according to claim 7, wherein said second domain comprises an amino acid sequence selected from the group consisting of:
    (a) an amino acid sequence of SEQ ID NO.: 22, 24, 26, 28, 30 or 32;
    (b) an amino acid sequence encoded by the nucleic acid sequence of SEQ ID NO.: 21, 23, 25, 27, 29 or 31; and
    (c) an amino acid sequence encoded by a nucleic acid sequence which is degenerate as a result of the genetic code to the nucleic acid sequence of any one of (b).

11. The bispecific single chain antibody construct according to claim 10, wherein said bispecific single chain antibody construct comprises an amino acid sequence selected from the group consisting of:
    (a) an amino acid sequence of SEQ ID NO.: 34 or 36;
    (b) an amino acid sequence encoded by the nucleic acid sequence of SEQ ID NO.: 33 or 35; and
    (c) an amino acid sequence encoded by a nucleic acid sequence which is degenerate as a result of the genetic code to the nucleic acid sequence of any one of (b).

12. The bispecific single chain antibody construct according to claim 4, wherein said antigen-binding site is humanized.

13. An isolated nucleic acid encoding the bispecific single chain antibody construct according to claim 1.

14. The nucleic acid of claim 13 comprising a nucleotide sequence selected from the group consisting of:
    (a) a nucleotide sequence encoding the mature form of a protein comprising the amino acid sequence selected from the group of SEQ ID NOs: 20, 34 and 36;
    (b) a nucleotide sequence comprising or consisting of a DNA sequence selected from the group of SEQ ID NOs: 19, 33 and 35; and
    (c) a nucleotide sequence which is degenerate as a result of the genetic code to a nucleotide sequence of any one of (a) or (b).

15. An isolated vector comprising the nucleic acid according to claim 13.

16. The isolated vector of claim 15, which further comprises a regulatory sequence operably linked to said nucleic acid.

17. The isolated vector of claim 15, wherein the vector is an expression vector.

18. An isolated host transformed or transfected with the nucleic acid of claim 13 or a vector comprising the nucleic acid.

19. A process for the production of a bispecific single chain antibody construct according to claim 1, said process comprising culturing an isolated host transformed or transfected with the nucleic acid of claim 13 or a vector comprising the nucleic acid under conditions allowing the expression of the bispecific single chain antibody construct and recovering the produced bispecific single chain antibody construct from the culture.

20. A composition comprising the bispecific single chain antibody construct according to claim 1 and, optionally, a proteinaceous compound capable of providing an activation signal for immune effector cells.

21. The composition of claim 20 which is a pharmaceutical composition further comprising suitable formulations of carrier, stabilizers and/or excipients.

22. The composition of claim 20 which is a diagnostic composition for detection of proliferative diseases, tumorous diseases, inflammatory diseases, immunological disorders, autoimmune diseases, infectious diseases, viral diseases, allergic reactions, parasitic reactions, graft-versus-host diseases or host-versus-graft diseases.

23. A kit comprising the bispecific single chain antibody construct according to claim 1.

\* \* \* \* \*

SEQUENCE LISTING

```
<160> NUMBER OF SEQ ID NOS: 40

<210> SEQ ID NO 1
<211> LENGTH: 318
<212> TYPE: DNA
<213> ORGANISM: Artificial Sequence
<220> FEATURE:
<223> OTHER INFORMATION: Description of Artificial Sequence: Synthetic
      OKT3 light chain

<400> SEQUENCE: 1
gacatccaga tgacccagtc tccatcctcc ctgtctgcat ctgtaggaga cagagtcacc      60
atcacttgca gtgcaagttc aagcgtaagc tacatgaatt ggtatcagca gacaccaggg     120
aaagccccta agagatggat ctatgacaca tccaaattgg cttctggggt cccatcaagg     180
ttcagtggca gtggatctgg gacagattac actttcacca tcagcagtct gcaacctgaa     240
gatattgcaa cttactactg tcaacagtgg agtagtaacc cttttacttt tggccagggg     300
accaagctgc agatcacc                                                   318

<210> SEQ ID NO 2
<211> LENGTH: 106
<212> TYPE: PRT
<213> ORGANISM: Artificial Sequence
<220> FEATURE:
<223> OTHER INFORMATION: Description of Artificial Sequence: Synthetic
      OKT3 VL

<400> SEQUENCE: 2

Asp Ile Gln Met Thr Gln Ser Pro Ser Ser Leu Ser Ala Ser Val Gly
```

```
                1               5                  10                 15
Asp Arg Val Thr Ile Thr Cys Ser Ala Ser Ser Ser Val Ser Tyr Met
                                20                 25                 30

Asn Trp Tyr Gln Gln Thr Pro Gly Lys Ala Pro Lys Arg Trp Ile Tyr
                35                 40                 45

Asp Thr Ser Lys Leu Ala Ser Gly Val Pro Ser Arg Phe Ser Gly Ser
            50                 55                 60

Gly Ser Gly Thr Asp Tyr Thr Phe Thr Ile Ser Ser Leu Gln Pro Glu
65                 70                 75                 80

Asp Ile Ala Thr Tyr Tyr Cys Gln Gln Trp Ser Ser Asn Pro Phe Thr
                    85                 90                 95

Phe Gly Gln Gly Thr Lys Leu Gln Ile Thr
                100                105

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
agagcaagtt caagcgtaag ctacatgaat                                     30

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ala Ser Ser Ser Val Ser Tyr Met Asn
1               5                  10

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      peptide

<400> SEQUENCE: 5
gacacatcca aagtggcttc t                                              21

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asp Thr Ser Lys Val Ala Ser
1               5

<210> SEQ ID NO 7
<211> LENGTH: 27
<212> TYPE: DNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 7
caacagtgga gtagtaaccc tctcact                                              27

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Gln Trp Ser Ser Asn Pro Leu Thr
1               5

<210> SEQ ID NO 9
<211> LENGTH: 318
<212> TYPE: DNA
<213> ORGANISM: Artificial Sequence
<220> FEATURE:
<223> OTHER INFORMATION: Description of Artificial Sequence: Synthetic
      CD3 VL

<400> SEQUENCE: 9
gacatccaga tgacccagtc tccatcctcc ctgtctgcat ctgtaggaga cagagtcacc           60
atcacttgca gagcaagttc aagcgtaagc tacatgaatt ggtatcagca gacaccaggg          120
aaagccccta agagatggat ctatgacaca tccaaagtgg cttctggggt cccatcaagg          180
ttcagtggca gtggatctgg gacagattac actttcacca tcagcagtct gcaacctgaa          240
gatattgcaa cttactactg tcaacagtgg agtagtaacc ctctcacttt tggccagggg          300
accaagctgc agatcacc                                                       318

<210> SEQ ID NO 10
<211> LENGTH: 106
<212> TYPE: PRT
<213> ORGANISM: Artificial Sequence
<220> FEATURE:
<223> OTHER INFORMATION: Description of Artificial Sequence: Synthetic
      CD3 VL

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
            20                  25                  30

Asn Trp Tyr Gln Gln Thr Pro Gly Lys Ala Pro Lys Arg Trp Ile Tyr
        35                  40                  45

Asp Thr Ser Lys Val Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser Asn Pro Leu Thr
                85                  90                  95

Phe Gly Gln Gly Thr Lys Leu Gln Ile Thr
            100                 105

<210> SEQ ID NO 11
<211> LENGTH: 357
<212> TYPE: DNA

<213> ORGANISM: Artificial Sequence
<220> FEATURE:
<223> OTHER INFORMATION: Description of Artificial Sequence: Synthetic CD3 VH

<400> SEQUENCE: 11

```
caggtgcagc tggtgcagtc tgggggaggc gtggtccagc ctggaggtc cctgagactc      60
tcctgtaagt cttctggata caccttcact aggtatacga tgcactggt ccgccaggct    120
ccagggaagg ggctggagtg gattggatac ataaatccta gccgtggtta tactaattat    180
aatcagaagg tgaaggaccg attcaccatc tccagagaca actccaagaa cacggccttt    240
ctgcaaatgg acagcctgag acccgaggac acgggtgtgt atttctgtgc gagatattat    300
gatgatcatt actgccttga ctactggggc cagggcaccc cggtcaccgt ctcctca       357
```

<210> SEQ ID NO 12
<211> LENGTH: 119
<212> TYPE: PRT
<213> ORGANISM: Artificial Sequence
<220> FEATURE:
<223> OTHER INFORMATION: Description of Artificial Sequence: Synthetic CD3 VH

<400> SEQUENCE: 12

```
Gln Val Gln Leu Val Gln Ser Gly Gly Gly Val Val Gln Pro Gly Arg
1               5                   10                  15
Ser Leu Arg Leu Ser Cys Lys Ser Ser Gly Tyr Thr Phe Thr Arg Tyr
            20                  25                  30
Thr Met His Trp Val Arg Gln Ala Pro Gly Lys Gly Leu Glu Trp Ile
        35                  40                  45
Gly Tyr Ile Asn Pro Ser Arg Gly Tyr Thr Asn Tyr Asn Gln Lys Val
    50                  55                  60
Lys Asp Arg Phe Thr Ile Ser Arg Asp Asn Ser Lys Asn Thr Ala Phe
65                  70                  75                  80
Leu Gln Met Asp Ser Leu Arg Pro Glu Asp Thr Gly Val Tyr Phe Cys
                85                  90                  95
Ala Arg Tyr Tyr Asp Asp His Tyr Cys Leu Asp Tyr Trp Gly Gln Gly
            100                 105                 110
Thr Pro Val Thr Val Ser Ser
        115
```

<210> SEQ ID NO 13
<211> LENGTH: 729
<212> TYPE: DNA
<213> ORGANISM: Artificial Sequence
<220> FEATURE:
<223> OTHER INFORMATION: Description of Artificial Sequence: Synthetic CD3 VH-VL

<400> SEQUENCE: 13

```
caggtgcagc tggtgcagtc tgggggaggc gtggtccagc ctggaggtc cctgagactc      60
tcctgtaagt cttctggata caccttcact aggtatacga tgcactgggt ccgccaggct    120
ccagggaagg ggctggagtg gattggatac ataaatccta gccgtggtta tactaattat    180
aatcagaagg tgaaggaccg attcaccatc tccagagaca actccaagaa cacggccttt    240
ctgcaaatgg acagcctgag acccgaggac acgggtgtgt atttctgtgc gagatattat    300
gatgatcatt actgccttga ctattggggc cagggcaccc cggtcaccgt ctcctcagtc    360
gaaggtggaa gtgagggttc tggtggaagt ggaggttcag gtggagtgga cgacatccag    420
atgacccagt ctccatcctc cctgtctgca tctgtaggag acagagtcac catcacttgc    480
```

```
agagcaagtt caagcgtaag ctacatgaat tggtatcagc agacaccagg gaaagcccct    540
aagagatgga tctatgacac atccaaagtg gcttctgggg tcccatcaag gttcagtggc    600
agtggatctg ggacagatta cactttcacc atcagcagtc tgcaacctga agatattgca    660
acttactact gtcaacagtg gagtagtaac cctctcactt ttggccaggg gaccaagctg    720
cagatcacc                                                            729
```

```
<210> SEQ ID NO 14
<211> LENGTH: 243
<212> TYPE: PRT
<213> ORGANISM: Artificial Sequence
<220> FEATURE:
<223> OTHER INFORMATION: Description of Artificial Sequence: Synthetic
      CD3 VH-VL

<400> SEQUENCE: 14
```

Gln Val Gln Leu Val Gln Ser Gly Gly Gly Val Val Gln Pro Gly Arg
1               5                   10                  15

Ser Leu Arg Leu Ser Cys Lys Ser Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Val
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Cys Leu Asp Tyr Trp Gly Gln Gly
            100                 105                 110

Thr Pro Val Thr Val Ser Ser Val Glu Gly Gly Ser Gly Gly Ser Gly
        115                 120                 125

Gly Ser Gly Gly Ser Gly Gly Val Asp Asp Ile Gln Met Thr Gln Ser
    130                 135                 140

Pro Ser Ser Leu Ser Ala Ser Val Gly Asp Arg Val Thr Ile Thr Cys
145                 150                 155                 160

Arg Ala Ser Ser Ser Val Ser Tyr Met Asn Trp Tyr Gln Gln Thr Pro
                165                 170                 175

Gly Lys Ala Pro Lys Arg Trp Ile Tyr Asp Thr Ser Lys Val Ala Ser
            180                 185                 190

Gly Val Pro Ser Arg Phe Ser Gly Ser Gly Ser Gly Thr Asp Tyr Thr
        195                 200                 205

Phe Thr Ile Ser Ser Leu Gln Pro Glu Asp Ile Ala Thr Tyr Tyr Cys
    210                 215                 220

Gln Gln Trp Ser Ser Asn Pro Leu Thr Phe Gly Gln Gly Thr Lys Leu
225                 230                 235                 240

Gln Ile Thr

```
<210> SEQ ID NO 15
<211> LENGTH: 372
<212> TYPE: DNA
<213> ORGANISM: Artificial Sequence
<220> FEATURE:
<223> OTHER INFORMATION: Description of Artificial Sequence: Synthetic
      CD19 VH

<400> SEQUENCE: 15
```

```
caggtgcagc tgcagcagtc tggggctgag ctggtgaggc ctgggtcctc agtgaagatt    60
tcctgcaagg cttctggcta tgcattcagt agctactgga tgaactgggt gaagcagagg   120
cctggacagg gtcttgagtg gattggacag atttggcctg agatggtga tactaactac    180 aatgaaagt tcaagggtaa agccactctg actgcagacg aatcctccag cacagcctac    240
atgcaactca gcagcctagc atctgaggac tctgcggtct atttctgtgc aagacgggag   300
actacgacgg taggccgtta ttactatgct atggactact ggggccaagg gaccacggtc   360
accgtctcct cc                                                       372

<210> SEQ ID NO 16
<211> LENGTH: 124
<212> TYPE: PRT
<213> ORGANISM: Artificial Sequence
<220> FEATURE:
<223> OTHER INFORMATION: Description of Artificial Sequence: Synthetic
      CD19 VH

<400> SEQUENCE: 16

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser
        115                 120

<210> SEQ ID NO 17
<211> LENGTH: 333
<212> TYPE: DNA
<213> ORGANISM: Artificial Sequence
<220> FEATURE:
<223> OTHER INFORMATION: Description of Artificial Sequence: Synthetic
      CD19 VL

<400> SEQUENCE: 17
gatatccagc tgacccagtc tccagcttct ttggctgtgt ctctagggca gagggccacc    60
atctcctgca aggccagcca agtgttgat tatgatggtg atagttattt gaactggtac    120
caacagattc caggacagcc acccaaactc ctcatctatg atgcatccaa tctagtttct    180
gggatcccac ccaggtttag tggcagtggg tctgggacag acttcaccct caacatccat    240
cctgtggaga aggtggatgc tgcaacctat cactgtcagc aaagtactga ggatccgtgg    300
acgttcggtg gagggaccaa gctcgagatc aaa                                333

<210> SEQ ID NO 18
<211> LENGTH: 111
<212> TYPE: PRT
<213> ORGANISM: Artificial Sequence
<220> FEATURE:
<223> OTHER INFORMATION: Description of Artificial Sequence: Synthetic
      CD19 VL
```

<400> SEQUENCE: 18

```
Asp Ile Gln Leu Thr Gln Ser Pro Ala Ser Leu Ala Val Ser Leu Gly
 1               5                  10                  15

Gln Arg Ala Thr Ile Ser Cys Lys Ala Ser Gln Ser Val Asp Tyr Asp
             20                  25                  30

Gly Asp Ser Tyr Leu Asn Trp Tyr Gln Gln Ile Pro Gly Gln Pro Pro
         35                  40                  45

Lys Leu Leu Ile Tyr Asp Ala Ser Asn Leu Val Ser Gly Ile Pro Pro
     50                  55                  60

Arg Phe Ser Gly Ser Gly Ser Gly Thr Asp Phe Thr Leu Asn Ile His
 65                  70                  75                  80

Pro Val Glu Lys Val Asp Ala Ala Thr Tyr His Cys Gln Gln Ser Thr
                 85                  90                  95

Glu Asp Pro Trp Thr Phe Gly Gly Gly Thr Lys Leu Glu Ile Lys
            100                 105                 110
```

<210> SEQ ID NO 19
<211> LENGTH: 1504
<212> TYPE: DNA
<213> ORGANISM: Artificial Sequence
<220> FEATURE:
<223> OTHER INFORMATION: Description of Artificial Sequence: Synthetic anti-CD3

<400> SEQUENCE: 19

```
tgtacactcc gatatccagc tgacccagtc tccagcttct ttggctgtgt ctctagggca    60
gagggccacc atctcctgca aggccagcca aagtgttgat tatgatggtg atagttattt   120
gaactggtac caacagattc caggacagcc acccaaactc ctcatctatg atgcatccaa   180
tctagtttct gggatcccac ccaggtttag tggcagtggg tctgggacag acttcaccct   240
caacatccat cctgtggaga aggtggatgc tgcaacctat cactgtcagc aaagtactga   300
ggatccgtgg acgttcggtg agggaccaag ctcgagatc aaaggtggtg gtggttctgg   360
cggcggcggc tccggtggtg gtggttctca ggtgcagctg cagcagtctg ggctgagct   420
ggtgaggcct gggtcctcag tgaagatttc ctgcaaggct tctggctatg cattcagtag   480
ctactggatg aactgggtga agcagaggcc tggacagggt cttgagtgga ttggacagat   540
ttggcctgga gatggtgata ctaactacaa tggaaagttc aagggtaaag ccactctgac   600
tgcagacgaa tcctccagca cagcctacat gcaactcagc agcctagcat ctgaggactc   660
tgcggtctat ttctgtgcaa gacgggagac tacgacggta ggccgttatt actatgctat   720
ggactactgg ggccaaggga ccacggtcac cgtctcctcc ggaggtggtg gctcccaggt   780
gcagctggtg cagtctgggg gaggcgtggt ccagcctggg aggtccctga gactctcctg   840
taagtcttct ggatacacct tcactaggta tacgatgcac tgggtccgcc aggctccagg   900
gaaggggctg gagtggattg gatacataaa tcctagccgt ggttatacta attataatca   960
gaaggtgaag gaccgattca ccatctccag agacaactcc aagaacacgg cctttctgca  1020
aatggacagc ctgagacccg aggacacggg tgtgtatttc tgtgcgagat attatgatga  1080
tcattactgc cttgactatt ggggccaggg caccccggtc accgtctcct cagtcgaagg  1140
tggaagtgga ggttctggtg aagtggaggt tcaggtgga gtggacgaca tccagatgac  1200
ccagtctcca tcctccctgt ctgcatctgt aggagacaga gtcaccatca cttgcagagc  1260
aagttcaagc gtaagctaca tgaattggta tcagcagaca ccaggaaag ccctaagag  1320
atggatctat gacacatcca agtggcttc tgggtcccca tcaaggttca gtggcagtgg  1380
```

```
atctgggaca gattacactt tcaccatcag cagtctgcaa cctgaagata ttgcaactta    1440
ctactgtcaa cagtggagta gtaaccctct cactttggc  caggggacca agctgcagat    1500
cacc                                                                 1504
```

<210> SEQ ID NO 20
<211> LENGTH: 498
<212> TYPE: PRT
<213> ORGANISM: Artificial Sequence
<220> FEATURE:
<223> OTHER INFORMATION: Description of Artificial Sequence: Synthetic anti-CD3

<400> SEQUENCE: 20

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Gln
                245                 250                 255

Val Gln Leu Val Gln Ser Gly Gly Gly Val Val Gln Pro Gly Arg Ser
            260                 265                 270

Leu Arg Leu Ser Cys Lys Ser Ser Gly Tyr Thr Phe Thr Arg Tyr Thr
        275                 280                 285

Met His Trp Val Arg Gln Ala Pro Gly Lys Gly Leu Glu Trp Ile Gly
    290                 295                 300

Tyr Ile Asn Pro Ser Arg Gly Tyr Thr Asn Tyr Asn Gln Lys Val Lys
305                 310                 315                 320

Asp Arg Phe Thr Ile Ser Arg Asp Asn Ser Lys Asn Thr Ala Phe Leu
                325                 330                 335
```

```
Gln Met Asp Ser Leu Arg Pro Glu Asp Thr Gly Val Tyr Phe Cys Ala
            340                 345                 350

Arg Tyr Tyr Asp Asp His Tyr Cys Leu Asp Tyr Trp Gly Gln Gly Thr
            355                 360                 365

Pro Val Thr Val Ser Ser Val Glu Gly Gly Ser Gly Gly Ser Gly Gly
            370                 375                 380

Ser Gly Ser Gly Gly Val Asp Asp Ile Gln Met Thr Gln Ser Pro
385                 390                 395                 400

Ser Ser Leu Ser Ala Ser Val Gly Asp Arg Val Thr Ile Thr Cys Arg
                405                 410                 415

Ala Ser Ser Val Ser Tyr Met Asn Trp Tyr Gln Gln Thr Pro Gly
                420                 425                 430

Lys Ala Pro Lys Arg Trp Ile Tyr Asp Thr Ser Lys Val Ala Ser Gly
                435                 440                 445

Val Pro Ser Arg Phe Ser Gly Ser Gly Ser Gly Thr Asp Tyr Thr Phe
            450                 455                 460

Thr Ile Ser Ser Leu Gln Pro Glu Asp Ile Ala Thr Tyr Tyr Cys Gln
465                 470                 475                 480

Gln Trp Ser Ser Asn Pro Leu Thr Phe Gly Gly Gly Thr Lys Leu Gln
                485                 490                 495

Ile Thr

<210> SEQ ID NO 21
<211> LENGTH: 360
<212> TYPE: DNA
<213> ORGANISM: Artificial Sequence
<220> FEATURE:
<223> OTHER INFORMATION: Description of Artificial Sequence: Synthetic
      5-10 VH

<400> SEQUENCE: 21
gaggtgcagc tgctcgagca gtctggagct gagctggtaa ggcctgggac ttcagtgaag      60
atatcctgca aggcttctgg atacgccttc actaactact ggctaggttg ggtaaagcag     120
aggcctggac atggacttga gtggattgga gatattttcc ctggaagtgg taatatccac     180
tacaatgaga agttcaaggg caaagccaca ctgactgcag acaaatcttc gagcacagcc     240
tatatgcagc tcagtagcct gacatttgag gactctgctg tctatttctg tgcaagactg     300
aggaactggg acgagcctat ggactactgg ggccaaggga ccacggtcac cgtctcctcc     360

<210> SEQ ID NO 22
<211> LENGTH: 120
<212> TYPE: PRT
<213> ORGANISM: Artificial Sequence
<220> FEATURE:
<223> OTHER INFORMATION: Description of Artificial Sequence: Synthetic
      5-10 VH

<400> SEQUENCE: 22

Glu Val Gln Leu Leu Glu Gln Ser Gly Ala Glu Leu Val Arg Pro Gly
1               5                   10                  15

Thr Ser Val Lys Ile Ser Cys Lys Ala Ser Gly Tyr Ala Phe Thr Asn
                20                  25                  30

Tyr Trp Leu Gly Trp Val Lys Gln Arg Pro Gly His Gly Leu Glu Trp
            35                  40                  45

Ile Gly Asp Ile Phe Pro Gly Ser Gly Asn Ile His Tyr Asn Glu Lys
        50                  55                  60

Phe Lys Gly Lys Ala Thr Leu Thr Ala Asp Lys Ser Ser Ser Thr Ala
```

```
                65                  70                  75                  80
Tyr Met Gln Leu Ser Ser Leu Thr Phe Glu Asp Ser Ala Val Tyr Phe
                        85                  90                  95

Cys Ala Arg Leu Arg Asn Trp Asp Glu Pro Met Asp Tyr Trp Gly Gln
                100                 105                 110

Gly Thr Thr Val Thr Val Ser Ser
                115                 120

<210> SEQ ID NO 23
<211> LENGTH: 339
<212> TYPE: DNA
<213> ORGANISM: Artificial Sequence
<220> FEATURE:
<223> OTHER INFORMATION: Description of Artificial Sequence: Synthetic
      5-10 VL

<400> SEQUENCE: 23
gagctcgtga tgacacagtc tccatcctcc ctgactgtga cagcaggaga gaaggtcact      60
atgagctgca agtccagtca gagtctgtta aacagtggaa atcaaaagaa ctacttgacc     120
tggtaccagc agaaaccagg gcagcctcct aaactgttga tctactgggc atccactagg     180
gaatctgggg tccctgatcg cttcacaggc agtggatctg gaacagattt cactctcacc     240
atcagcagtg tgcaggctga agacctggca gtttattact gtcagaatga ttatagttat     300
ccgctcacgt tcggtgctgg gaccaagctt gagatcaaa                            339

<210> SEQ ID NO 24
<211> LENGTH: 113
<212> TYPE: PRT
<213> ORGANISM: Artificial Sequence
<220> FEATURE:
<223> OTHER INFORMATION: Description of Artificial Sequence: Synthetic
      5-10 VL

<400> SEQUENCE: 24

Glu Leu Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
                20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Ile
                100                 105                 110

Lys

<210> SEQ ID NO 25
<211> LENGTH: 360
<212> TYPE: DNA
<213> ORGANISM: Artificial Sequence
<220> FEATURE:
<223> OTHER INFORMATION: Description of Artificial Sequence: Synthetic
      3-1 VH

<400> SEQUENCE: 25
gaggtgcagc tgctcgagca gtctggagct gagctggtga aacctggggc ctcagtgaag      60
```

```
atatcctgca aggcttctgg atacgccttc actaactact ggctaggttg ggtaaagcag    120
aggcctggac atggacttga gtggattgga gatcttttcc ctggaagtgg taatactcac    180
tacaatgaga ggttcagggg caaagccaca ctgactgcag acaaatcctc gagcacagcc    240
tttatgcagc tcagtagcct gacatctgag gactctgctg tctatttctg tgcaagattg    300
aggaactggg acgaggctat ggactactgg ggccaaggga ccacggtcac cgtctcctcc    360
```

```
<210> SEQ ID NO 26
<211> LENGTH: 120
<212> TYPE: PRT
<213> ORGANISM: Artificial Sequence
<220> FEATURE:
<223> OTHER INFORMATION: Description of Artificial Sequence: Synthetic
      3-1 VH

<400> SEQUENCE: 26

Glu Val Gln Leu Leu Glu Gln Ser Gly Ala Glu Leu Val Lys Pro Gly
1               5                   10                  15

Ala Ser Val Lys Ile Ser Cys Lys Ala Ser Gly Tyr Ala Phe Thr Asn
                20                  25                  30

Tyr Trp Leu Gly Trp Val Lys Gln Arg Pro Gly His Gly Leu Glu Trp
            35                  40                  45

Ile Gly Asp Leu Phe Pro Gly Ser Gly Asn Thr His Tyr Asn Glu Arg
        50                  55                  60

Phe Arg Gly Lys Ala Thr Leu Thr Ala Asp Lys Ser Ser Ser Thr Ala
65                  70                  75                  80

Phe Met Gln Leu Ser Ser Leu Thr Ser Glu Asp Ser Ala Val Tyr Phe
                85                  90                  95

Cys Ala Arg Leu Arg Asn Trp Asp Glu Ala Met Asp Tyr Trp Gly Gln
            100                 105                 110

Gly Thr Thr Val Thr Val Ser Ser
        115                 120
```

```
<210> SEQ ID NO 27
<211> LENGTH: 321
<212> TYPE: DNA
<213> ORGANISM: Artificial Sequence
<220> FEATURE:
<223> OTHER INFORMATION: Description of Artificial Sequence: Synthetic
      3-1 VL

<400> SEQUENCE: 27
gagctcgtca tgacccagtc tccatcttat cttgctgcat ctcctggaga aaccattact    60
attaattgca gggcaagtaa gagcattagc aaatatttag cctggtatca agagaaacct    120
gggaaaacta ataagcttct tatctactct ggatccactt tgcaatctgg aattccatca    180
aggttcagtg gcagtggatc tggtacagat ttcactctca ccatcagtag cctggagcct    240
gaagattttg caatgtatta ctgtcaacag cataatgaat atccgtacac gttcggaggg    300
gggaccaagc ttgagatcaa a                                              321
```

```
<210> SEQ ID NO 28
<211> LENGTH: 107
<212> TYPE: PRT
<213> ORGANISM: Artificial Sequence
<220> FEATURE:
<223> OTHER INFORMATION: Description of Artificial Sequence: Synthetic
      3-1 VL

<400> SEQUENCE: 28
```

```
Glu Leu Val Met Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Tyr
                85                  90                  95

Thr Phe Gly Gly Gly Thr Lys Leu Glu Ile Lys
            100                 105
```

<210> SEQ ID NO 29
<211> LENGTH: 372
<212> TYPE: DNA
<213> ORGANISM: Artificial Sequence
<220> FEATURE:
<223> OTHER INFORMATION: Description of Artificial Sequence: Synthetic
      4-7 VH

<400> SEQUENCE: 29

```
gaggtgcagc tgctcgagca gtctggagct gagctggcga ggcctggggc ttcagtgaag    60
ctgtcctgca aggcttctgg ctacaccttc acaaactatg gtttaagctg ggtgaagcag   120
aggcctggac aggtccttga gtggattgga gaggtttatc ctagaattgg taatgcttac   180
tacaatgaga agttcaaggg caaggccaca ctgactgcag acaaatcctc cagcacagcg   240
tccatggagc tccgcagcct gacctctgag gactctgcgg tctatttctg tgcaagacgg   300
ggatcctacg atactaacta cgactggtac ttcgatgtct ggggccaagg gaccacggtc   360
accgtctcct cc                                                      372
```

<210> SEQ ID NO 30
<211> LENGTH: 124
<212> TYPE: PRT
<213> ORGANISM: Artificial Sequence
<220> FEATURE:
<223> OTHER INFORMATION: Description of Artificial Sequence: Synthetic
      4-7 VH

<400> SEQUENCE: 30

```
Glu Val Gln Leu Leu Glu Gln Ser Gly Ala Glu Leu Ala Arg Pro Gly
1               5                   10                  15

Ala Ser Val Lys Leu Ser Cys Lys Ala Ser Gly Tyr Thr Phe Thr Asn
            20                  25                  30

Tyr Gly Leu Ser Trp Val Lys Gln Arg Pro Gly Gln Val Leu Glu Trp
        35                  40                  45

Ile Gly Glu Val Tyr Pro Arg Ile Gly Asn Ala Tyr Tyr Asn Glu Lys
    50                  55                  60

Phe Lys Gly Lys Ala Thr Leu Thr Ala Asp Lys Ser Ser Ser Thr Ala
65                  70                  75                  80

Ser Met Glu Leu Arg Ser Leu Thr Ser Glu Asp Ser Ala Val Tyr Phe
                85                  90                  95

Cys Ala Arg Arg Gly Ser Tyr Asp Thr Asn Tyr Asp Trp Tyr Phe Asp
            100                 105                 110

Val Trp Gly Gln Gly Thr Thr Val Thr Val Ser Ser
        115                 120
```

```
<210> SEQ ID NO 31
<211> LENGTH: 336
<212> TYPE: DNA
<213> ORGANISM: Artificial Sequence
<220> FEATURE:
<223> OTHER INFORMATION: Description of Artificial Sequence: Synthetic
      4-7 VL

<400> SEQUENCE: 31
gagctcgtga tgacccagac tccactctcc ctgcctgtca gtcttggaga tcaagcctcc      60
atctcttgca gatctagtca gagccttgta cacagtaatg aaacacccta tttacattgg    120
tacctgcaga agccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tatttctgct ctcaaagtac acatgttccg    300
tacacgttcg aggggggac caagcttgag atcaaa                              336

<210> SEQ ID NO 32
<211> LENGTH: 112
<212> TYPE: PRT
<213> ORGANISM: Artificial Sequence
<220> FEATURE:
<223> OTHER INFORMATION: Description of Artificial Sequence: Synthetic
      4-7 VL

<400> SEQUENCE: 32

Glu Leu Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
            100                 105                 110

<210> SEQ ID NO 33
<211> LENGTH: 1470
<212> TYPE: DNA
<213> ORGANISM: Artificial Sequence
<220> FEATURE:
<223> OTHER INFORMATION: Description of Artificial Sequence: Synthetic
      anti-CD3

<400> SEQUENCE: 33
gagctcgtca tgacccagtc tccatcttat cttgctgcat ctcctggaga aaccattact     60
attaattgca gggcaagtaa gagcattagc aaatatttag cctggtatca agagaaacct    120
gggaaaacta taagcttct tatctactct ggatccactt tgcaatctgg aattccatca    180
aggttcagtg gcagtggatc tggtacagat ttcactctca ccatcagtag cctggagcct    240
gaagattttg caatgtatta ctgtcaacag cataatgaat atccgtacac gttcggaggg    300
gggaccaagc ttgagatcaa aggtggtggt ggttctggcg gcggcggctc cggtggtggt    360
ggttctgagg tgcagctgct cgagcagtct ggagctgagc tggtgaaacc tgggcctca    420
```

-continued

```
gtgaagatat cctgcaaggc ttctggatac gccttcacta actactggct aggttgggta      480
aagcagaggc ctggacatgg acttgagtgg attggagatc ttttccctgg aagtggtaat      540
actcactaca atgagaggtt caggggcaaa gccacactga ctgcagacaa atcctcgagc      600
acagccttta tgcagctcag tagcctgaca tctgaggact ctgctgtcta tttctgtgca      660
agattgagga actgggacga ggctatggac tactggggcc aagggaccac ggtcaccgtc      720
tcctccggag gtggtggatc ccaggtgcag ctggtgcagt ctggggagg cgtggtccag       780 cctgggaggt ccctgagact ctcctgtaag tcttctggat acaccttcac taggtatacg      840
atgcactggg tccgccaggc tccagggaag gggctggagt ggattggata cataaatcct      900
agccgtggtt atactaatta taatcagaag gtgaaggacc gattcaccat ctccagagac      960
aactccaaga acacggcctt tctgcaaatg gacagcctga cccgagga cacgggtgtg       1020 tatttctgtg cgagatatta tgatgatcat tactgccttg actattgggg ccagggcacc     1080
ccggtcaccg tctcctcagt cgaaggtgga agtggaggtt ctggtggaag tggaggttca     1140
ggtggagtgg acgacatcca gatgacccag tctccatcct ccctgtctgc atctgtagga     1200
gacagagtca ccatcacttg cagagcaagt tcaagcgtaa gctacatgaa ttggtatcag     1260
cagacaccag ggaaagcccc taagagatgg atctatgaca catccaaagt ggcttctggg     1320
gtcccatcaa ggttcagtgg cagtggatct gggacagatt acactttcac catcagcagt     1380
ctgcaacctg aagatattgc aacttactac tgtcaacagt ggagtagtaa ccctctcact     1440
tttggccagg ggaccaagct gcagatcacc                                      1470
```

```
<210> SEQ ID NO 34
<211> LENGTH: 490
<212> TYPE: PRT
<213> ORGANISM: Artificial Sequence
<220> FEATURE:
<223> OTHER INFORMATION: Description of Artificial Sequence: Synthetic
      anti-CD3

<400> SEQUENCE: 34
```

Glu Leu Val Met Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Tyr
                85                  90                  95

Thr Phe Gly Gly Gly Thr Lys Leu Glu Ile Lys Gly Gly Gly Gly Ser
            100                 105                 110

Gly Gly Gly Gly Ser Gly Gly Gly Ser Glu Val Gln Leu Leu Glu
        115                 120                 125

Gln Ser Gly Ala Glu Leu Val Lys Pro Gly Ala Ser Val Lys Ile Ser
    130                 135                 140

Cys Lys Ala Ser Gly Tyr Ala Phe Thr Asn Tyr Trp Leu Gly Trp Val
145                 150                 155                 160

Lys Gln Arg Pro Gly His Gly Leu Glu Trp Ile Gly Asp Leu Phe Pro
                165                 170                 175

Gly Ser Gly Asn Thr His Tyr Asn Glu Arg Phe Arg Gly Lys Ala Thr
            180                 185                 190

Leu Thr Ala Asp Lys Ser Ser Thr Ala Phe Met Gln Leu Ser Ser
        195                 200                 205

Leu Thr Ser Glu Asp Ser Ala Val Tyr Phe Cys Ala Arg Leu Arg Asn
210                 215                 220

Trp Asp Glu Ala Met Asp Tyr Trp Gly Gln Gly Thr Val Thr Val
225                 230                 235                 240

Ser Ser Gly Gly Gly Gly Ser Gln Val Gln Leu Val Gln Ser Gly Gly
            245                 250                 255

Gly Val Val Gln Pro Gly Arg Ser Leu Arg Leu Ser Cys Lys Ser Ser
            260                 265                 270

Gly Tyr Thr Phe Thr Arg Tyr Thr Met His Trp Val Arg Gln Ala Pro
            275                 280                 285

Gly Lys Gly Leu Glu Trp Ile Gly Tyr Ile Asn Pro Ser Arg Gly Tyr
            290                 295                 300

Thr Asn Tyr Asn Gln Lys Val Lys Asp Arg Phe Thr Ile Ser Arg Asp
305                 310                 315                 320

Asn Ser Lys Asn Thr Ala Phe Leu Gln Met Asp Ser Leu Arg Pro Glu
                325                 330                 335

Asp Thr Gly Val Tyr Phe Cys Ala Arg Tyr Tyr Asp Asp His Tyr Cys
            340                 345                 350

Leu Asp Tyr Trp Gly Gln Gly Thr Pro Val Thr Val Ser Ser Val Glu
            355                 360                 365

Gly Gly Ser Gly Gly Ser Gly Gly Ser Gly Gly Ser Gly Gly Val Asp
            370                 375                 380

Asp Ile Gln Met Thr Gln Ser Pro Ser Ser Leu Ser Ala Ser Val Gly
385                 390                 395                 400

Asp Arg Val Thr Ile Thr Cys Arg Ala Ser Ser Ser Val Ser Tyr Met
                405                 410                 415

Asn Trp Tyr Gln Gln Thr Pro Gly Lys Ala Pro Lys Arg Trp Ile Tyr
            420                 425                 430

Asp Thr Ser Lys Val Ala Ser Gly Val Pro Ser Arg Phe Ser Gly Ser
            435                 440                 445

Gly Ser Gly Thr Asp Tyr Thr Phe Thr Ile Ser Ser Leu Gln Pro Glu
            450                 455                 460

Asp Ile Ala Thr Tyr Tyr Cys Gln Gln Trp Ser Ser Asn Pro Leu Thr
465                 470                 475                 480

Phe Gly Gln Gly Thr Lys Leu Gln Ile Thr
                485                 490

<210> SEQ ID NO 35
<211> LENGTH: 1498
<212> TYPE: DNA
<213> ORGANISM: Artificial Sequence
<220> FEATURE:
<223> OTHER INFORMATION: Description of Artificial Sequence: Synthetic
      anti-CD3

<400> SEQUENCE: 35
tgtacactcc gagctcgtga tgacacagtc tccatcctcc ctgactgtga cagcaggaga     60
gaaggtcact atgagctgca agtccagtca gagtctgtta aacagtggaa atcaaaagaa    120
ctacttgacc tggtaccagc agaaaccagg gcagcctcct aaactgttga tctactgggc    180
atccactagg gaatctgggg tccctgatcg cttcacaggc agtggatctg gaacagattt    240

```
cactctcacc atcagcagtg tgcaggctga agacctggca gtttattact gtcagaatga    300
ttatagttat ccgctcacgt tcggtgctgg gaccaagctt gagatcaaag gtggtggtgg    360
ttctggcggc ggcggctccg gtggtggtgg ttctgaggtg cagctgctcg agcagtctgg    420
agctgagctg gtaaggcctg ggacttcagt gaagatatcc tgcaaggctt ctggatacgc    480
cttcactaac tactggctag gttgggtaaa gcagaggcct ggacatggac ttgagtggat    540
tggagatatt ttccctggaa gtggtaatat ccactacaat gagaagttca gggcaaagc    600 cacactgact gcagacaaat cttcgagcac agcctatatg cagctcagta gcctgacatt    660
tgaggactct gctgtctatt tctgtgcaag actgaggaac tgggacgagc ctatggacta    720
ctggggccaa gggaccacgg tcaccgtctc ctccggaggt ggtggctccc aggtgcagct    780
ggtgcagtct gggggaggcg tggtccagcc tgggaggtcc ctgagactct cctgtaagtc    840
ttctggatac accttcacta ggtatacgat gcactgggtc cgccaggctc agggaaggg    900 gctggagtgg attggataca taaatcctag ccgtggttat actaattata atcagaaggt    960
gaaggaccga ttcaccatct ccagagacaa ctccaagaac acggcctttc tgcaaatgga   1020
cagcctgaga cccgaggaca cgggtgtgta tttctgtgcg agatattatg atgatcatta   1080
ctgccttgac tattggggcc agggcacccc ggtcaccgtc tcctcagtcg aaggtggaag   1140
tggaggttct ggtggaagtg gaggttcagg tggagtggac gacatccaga tgacccagtc   1200
tccatcctcc ctgtctgcat ctgtaggaga cagagtcacc atcacttgca gagcaagttc   1260
aagcgtaagc tacatgaatt ggtatcagca gacaccaggg aaagccccta agagatggat   1320
ctatgacaca tccaaagtgg cttctggggt cccatcaagg ttcagtggca gtggatctgg   1380
gacagattac actttcacca tcagcagtct gcaacctgaa gatattgcaa cttactactg   1440
tcaacagtgg agtagtaacc ctctcacttt tggccagggg accaagctgc agatcacc    1498
```

<210> SEQ ID NO 36
<211> LENGTH: 496
<212> TYPE: PRT
<213> ORGANISM: Artificial Sequence
<220> FEATURE:
<223> OTHER INFORMATION: Description of Artificial Sequence: Synthetic
      anti-CD3

<400> SEQUENCE: 36

```
Glu Leu Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Ile
            100                 105                 110

Lys Gly Gly Gly Gly Ser Gly Gly Gly Gly Ser Gly Gly Gly Gly Ser
        115                 120                 125

Glu Val Gln Leu Leu Glu Gln Ser Gly Ala Glu Leu Val Arg Pro Gly
    130                 135                 140
```

-continued

```
Thr Ser Val Lys Ile Ser Cys Lys Ala Ser Gly Tyr Ala Phe Thr Asn
145                 150                 155                 160

Tyr Trp Leu Gly Trp Val Lys Gln Arg Pro Gly His Gly Leu Glu Trp
                165                 170                 175

Ile Gly Asp Ile Phe Pro Gly Ser Gly Asn Ile His Tyr Asn Glu Lys
            180                 185                 190

Phe Lys Gly Lys Ala Thr Leu Thr Ala Asp Lys Ser Ser Thr Ala
        195                 200                 205

Tyr Met Gln Leu Ser Ser Leu Thr Phe Glu Asp Ser Ala Val Tyr Phe
    210                 215                 220

Cys Ala Arg Leu Arg Asn Trp Asp Glu Pro Met Asp Tyr Trp Gly Gln
225                 230                 235                 240

Gly Thr Thr Val Thr Val Ser Ser Gly Gly Gly Gly Ser Gln Val Gln
                245                 250                 255

Leu Val Gln Ser Gly Gly Gly Val Val Gln Pro Gly Arg Ser Leu Arg
            260                 265                 270

Leu Ser Cys Lys Ser Ser Gly Tyr Thr Phe Thr Arg Tyr Thr Met His
        275                 280                 285

Trp Val Arg Gln Ala Pro Gly Lys Gly Leu Glu Trp Ile Gly Tyr Ile
    290                 295                 300

Asn Pro Ser Arg Gly Tyr Thr Asn Tyr Asn Gln Lys Val Lys Asp Arg
305                 310                 315                 320

Phe Thr Ile Ser Arg Asp Asn Ser Lys Asn Thr Ala Phe Leu Gln Met
                325                 330                 335

Asp Ser Leu Arg Pro Glu Asp Thr Gly Val Tyr Phe Cys Ala Arg Tyr
            340                 345                 350

Tyr Asp Asp His Tyr Cys Leu Asp Tyr Trp Gly Gln Gly Thr Pro Val
        355                 360                 365

Thr Val Ser Ser Val Glu Gly Gly Ser Gly Gly Ser Gly Gly Ser Gly
    370                 375                 380

Gly Ser Gly Gly Val Asp Asp Ile Gln Met Thr Gln Ser Pro Ser Ser
385                 390                 395                 400

Leu Ser Ala Ser Val Gly Asp Arg Val Thr Ile Thr Cys Arg Ala Ser
                405                 410                 415

Ser Ser Val Ser Tyr Met Asn Trp Tyr Gln Gln Thr Pro Gly Lys Ala
            420                 425                 430

Pro Lys Arg Trp Ile Tyr Asp Thr Ser Lys Val Ala Ser Gly Val Pro
        435                 440                 445

Ser Arg Phe Ser Gly Ser Gly Ser Gly Thr Asp Tyr Thr Phe Thr Ile
    450                 455                 460

Ser Ser Leu Gln Pro Glu Asp Ile Ala Thr Tyr Tyr Cys Gln Gln Trp
465                 470                 475                 480

Ser Ser Asn Pro Leu Thr Phe Gly Gln Gly Thr Lys Leu Gln Ile Thr
                485                 490                 495
```

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 37

```
Leu Glu Trp Ile Gly
1               5
```

```
<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ser Ala Ser Ser Ser Val Ser Tyr Met Asn
1               5                   10

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Asp Thr Ser Lys Leu Ala Ser
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gln Gln Trp Ser Ser Asn Pro Phe Thr
1               5
```